(12) United States Patent
Quiachon et al.

(10) Patent No.: US 6,235,050 B1
(45) Date of Patent: *May 22, 2001

(54) SYSTEM AND METHOD FOR INTRALUMINALLY DEPLOYING A BIFURCATED GRAFT

(75) Inventors: Dinah B. Quiachon, San Jose; Alec A. Piplani, Mountain View; Steve G. Baker, Sunnyvale; Ronald G. Williams, Menlo Park; Richard S. Williams, Sunnyvale; Kenneth L. Osborn, Mountain View; Ted W. Layman, Palo Alto; Peter K. Johansson, San Jose, all of CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/484,285

(22) Filed: Jan. 18, 2000

Related U.S. Application Data

(63) Continuation of application No. 08/996,330, filed on Dec. 22, 1997, now Pat. No. 6,039,758, which is a continuation of application No. 08/707,179, filed on Sep. 3, 1996, now Pat. No. 5,824,044, which is a continuation-in-part of application No. 08/241,476, filed on May 12, 1994, now Pat. No. 5,628,783.

(51) Int. Cl.[7] ............................... A61F 2/06; A61F 11/00
(52) U.S. Cl. .................. 623/1.11; 623/1.12; 606/108; 606/194; 606/198
(58) Field of Search ............................. 623/1.11, 1, 1.12; 606/108, 190, 194, 198

(56) References Cited

U.S. PATENT DOCUMENTS

| 3,657,744 | 4/1972 | Ersek . |
|---|---|---|
| 4,061,134 | 12/1977 | Samuels et al. . |
| 4,108,161 | 8/1978 | Samuels et al. . |

(List continued on next page.)

FOREIGN PATENT DOCUMENTS

| 0 461 791 A1 | 12/1991 | (EP) . |
|---|---|---|
| 0 508 473 A2 | 10/1992 | (EP) . |
| 0 539 237 A1 | 4/1993 | (EP) . |
| 0 637 454 A1 | 2/1995 | (EP) . |
| 0 646 365 A1 | 4/1995 | (EP) . |
| 0 684 022 A2 | 11/1995 | (EP) . |
| 1217402 | 3/1986 | (SU) . |
| 1318235 A1 | 6/1987 | (SU) . |
| 1389778A2 | 4/1988 | (SU) . |
| 1457921A1 | 2/1989 | (SU) . |
| 1482714A2 | 5/1989 | (SU) . |
| WO 95/01761 | 1/1995 | (WO) . |
| WO 95/16406 | 6/1995 | (WO) . |
| WO 96/18361 | 6/1996 | (WO) . |

OTHER PUBLICATIONS

Parodi, MD et al. Annuals of Vascular Surgery (1991); pp. 5/6:491–499, "Transfemoral Intraluminal Graft Implani Abdominal Aortic Aneurysms".

Chuter, BM, BS et al., Journal of Vascular Surgery (Aug. 1993); pp. 18/2:185–196, "Transfemoral Endovascular Aortic Graft Placement".

*Primary Examiner*—Gary Jackson
(74) *Attorney, Agent, or Firm*—Fulwider Patton Lee & Utecht, LLP

(57) ABSTRACT

An apparatus and method for repairing a vessel at a bifurcation using a multicapsule catheter having first, second and third capsules for releasably retaining each terminal end of a bifurcated graft. The method for repairing the vessel includes the steps of performing a surgical technique to gain remote access to the vessel, advancing the multicapsule catheter within the vessel and releasing the bifurcated graft within the vessel to thereby repair the vessel.

15 Claims, 19 Drawing Sheets

U.S. PATENT DOCUMENTS

| | | |
|---|---|---|
| 4,140,126 | 2/1979 | Choudhury . |
| 4,214,578 | 7/1980 | Sakura, Jr. . |
| 4,577,631 | 3/1986 | Kreamer . |
| 4,617,932 | 10/1986 | Kornberg . |
| 4,728,328 | 3/1988 | Hughes et al. . |
| 4,732,152 | 3/1988 | Wallsten et al. . |
| 4,739,762 | 4/1988 | Palmaz . |
| 4,787,899 | 11/1988 | Lazarus . |
| 4,793,348 | 12/1988 | Palmaz . |
| 4,795,458 | 1/1989 | Regan . |
| 4,830,003 | 5/1989 | Wolff et al. . |
| 4,899,732 | 2/1990 | Cohen . |
| 4,969,896 | 11/1990 | Shors . |
| 5,026,377 | 6/1991 | Burton et al. . |
| 5,047,050 | 9/1991 | Ardesani . |
| 5,078,726 | 1/1992 | Kreamer . |
| 5,104,399 | 4/1992 | Lazarus . |
| 5,122,154 | 6/1992 | Rhodes . |
| 5,123,917 | 6/1992 | Lee . |
| 5,160,341 * | 11/1992 | Brenneman et al. ............. 623/1 |
| 5,192,297 | 3/1993 | Hull . |
| 5,201,757 | 4/1993 | Heyn et al. . |
| 5,219,355 | 6/1993 | Parodi et al. . |
| 5,275,622 | 1/1994 | Lazarus et al. . |
| 5,287,824 | 2/1994 | Gianturco . |
| 5,316,023 | 5/1994 | Palmaz et al. . |
| 5,360,443 | 11/1994 | Barone et al. . |
| 5,387,235 | 2/1995 | Chuter et al. . |
| 5,395,334 | 3/1995 | Keith et al. . |
| 5,397,345 | 3/1995 | Lazarus . |
| 5,489,295 | 2/1996 | Piplani et al. . |
| 5,507,769 * | 4/1996 | Marin et al. ............. 606/198 |
| 5,628,783 * | 5/1997 | Quiachon et al. ............. 623/1 |
| 5,693,083 * | 12/1997 | Baker et al. ............. 623/1 |
| 5,709,713 * | 1/1998 | Evans et al. ............. 623/1 |
| 5,824,044 * | 10/1998 | Quiachon et al. ............. 623/1 |

* cited by examiner

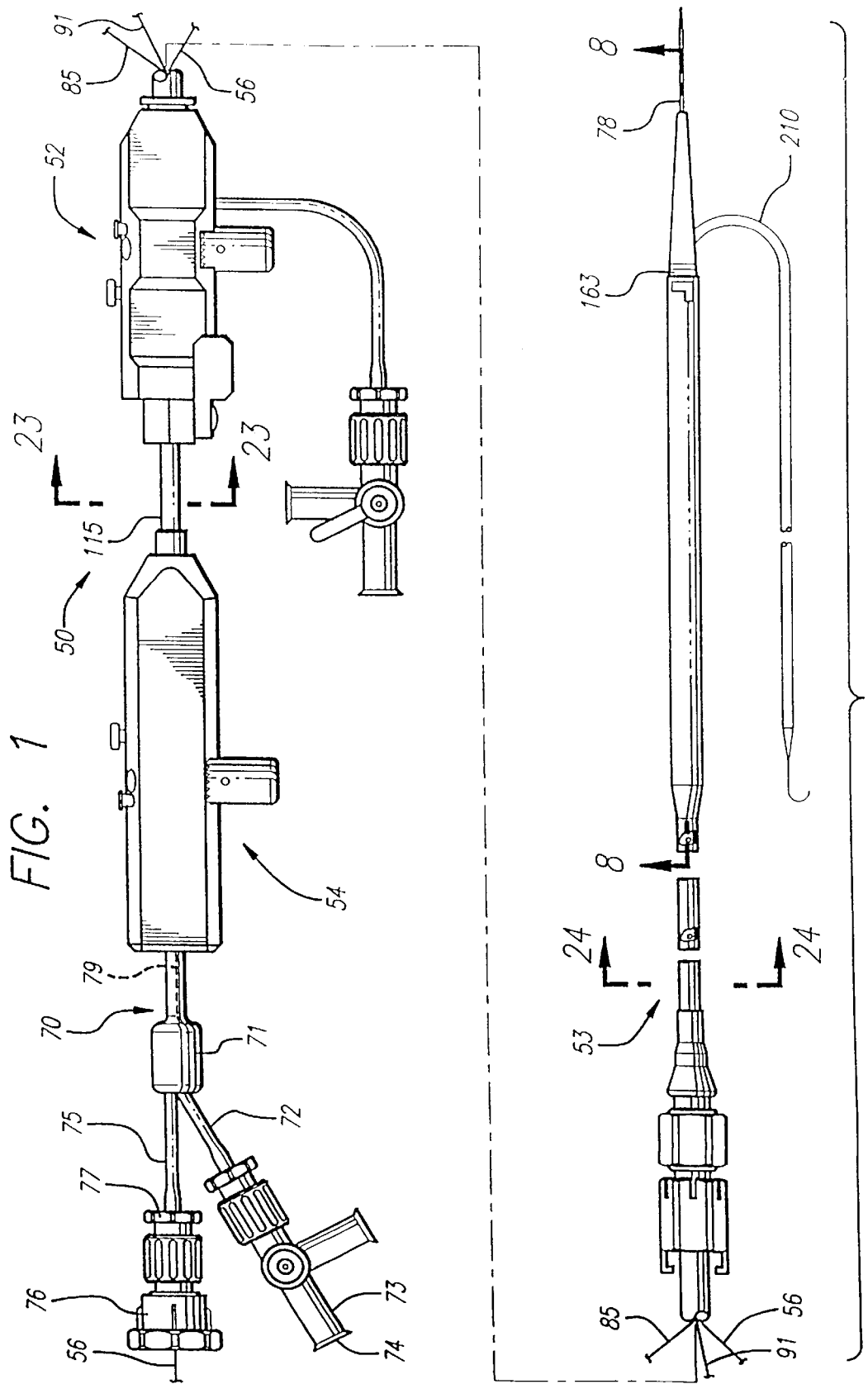

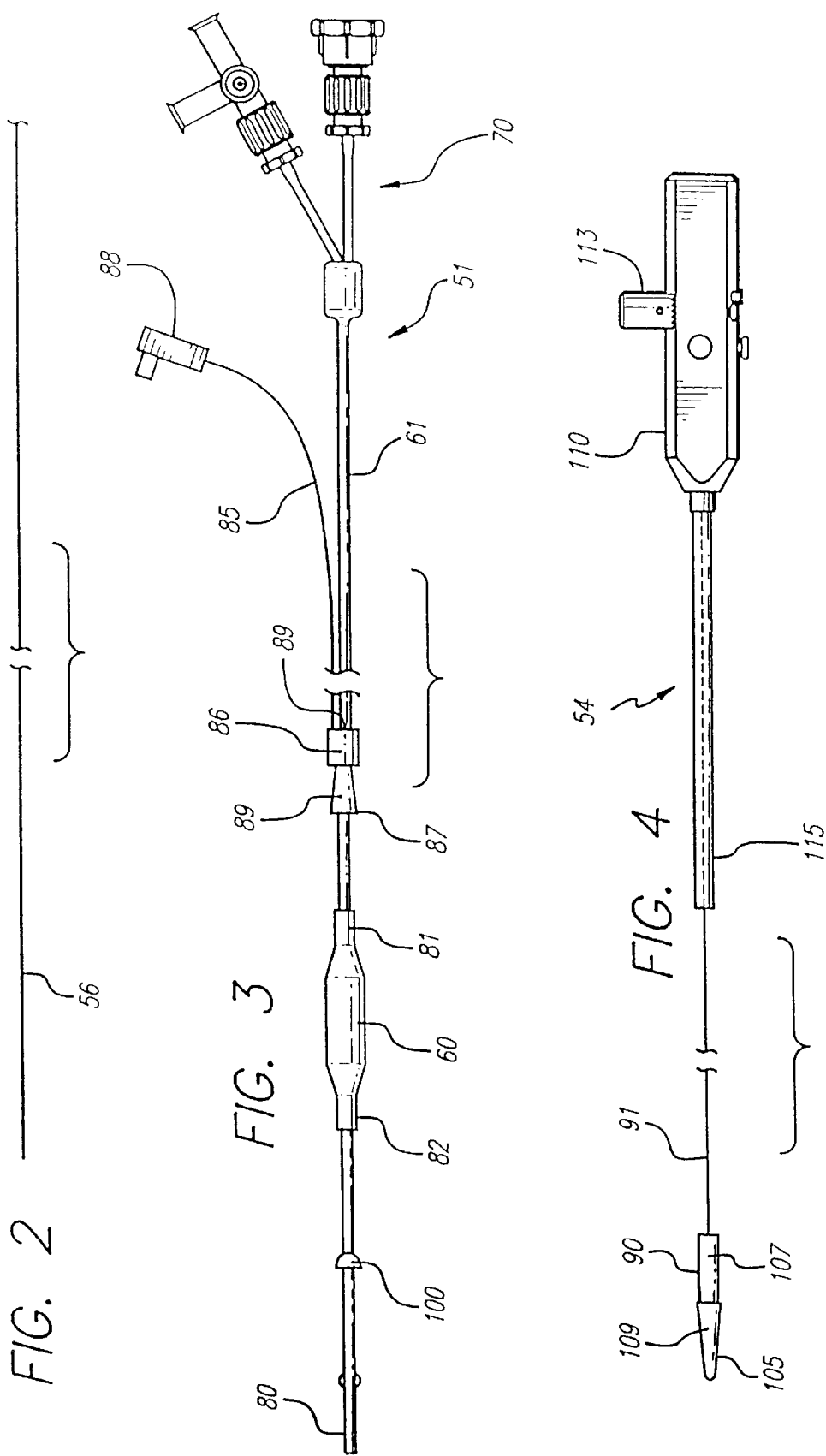

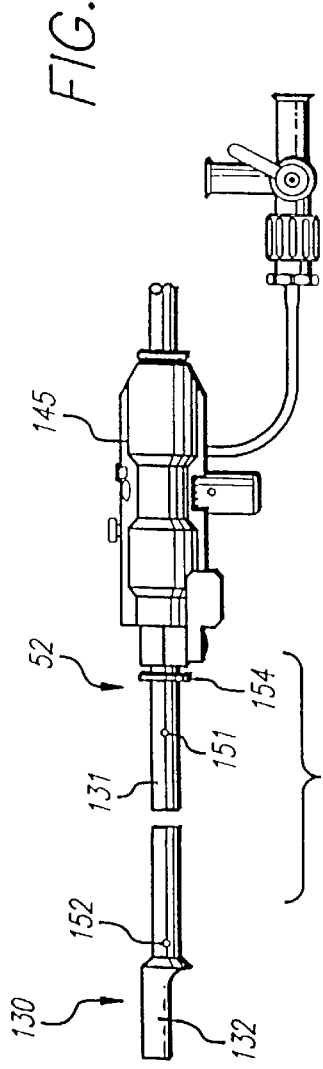
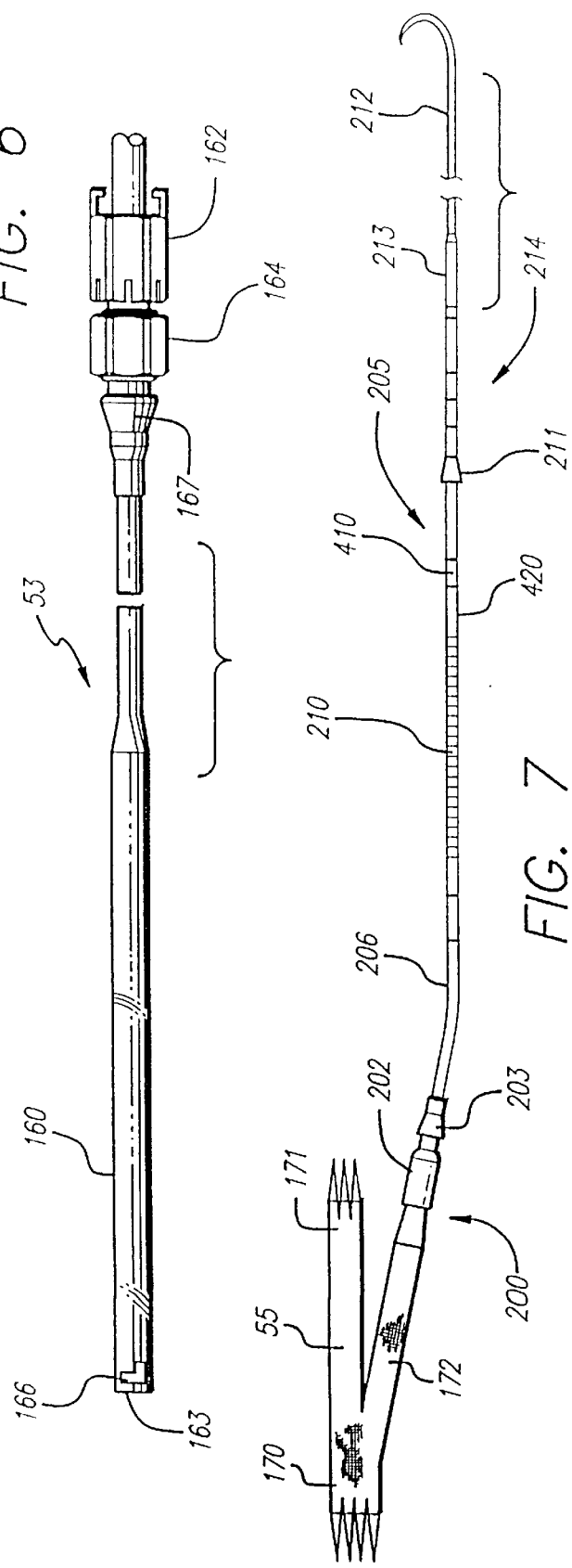

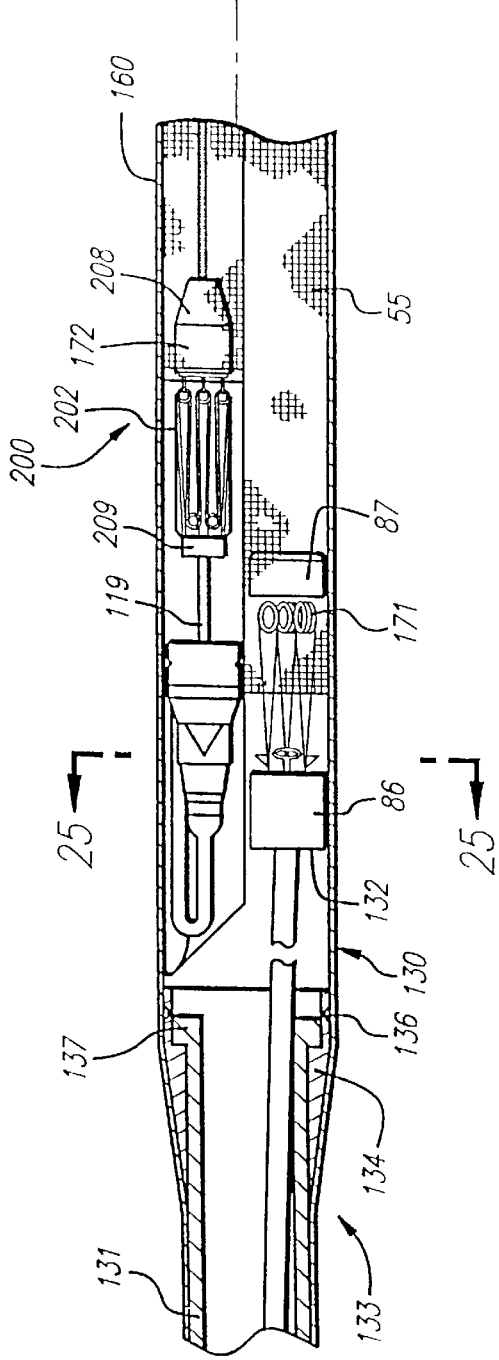
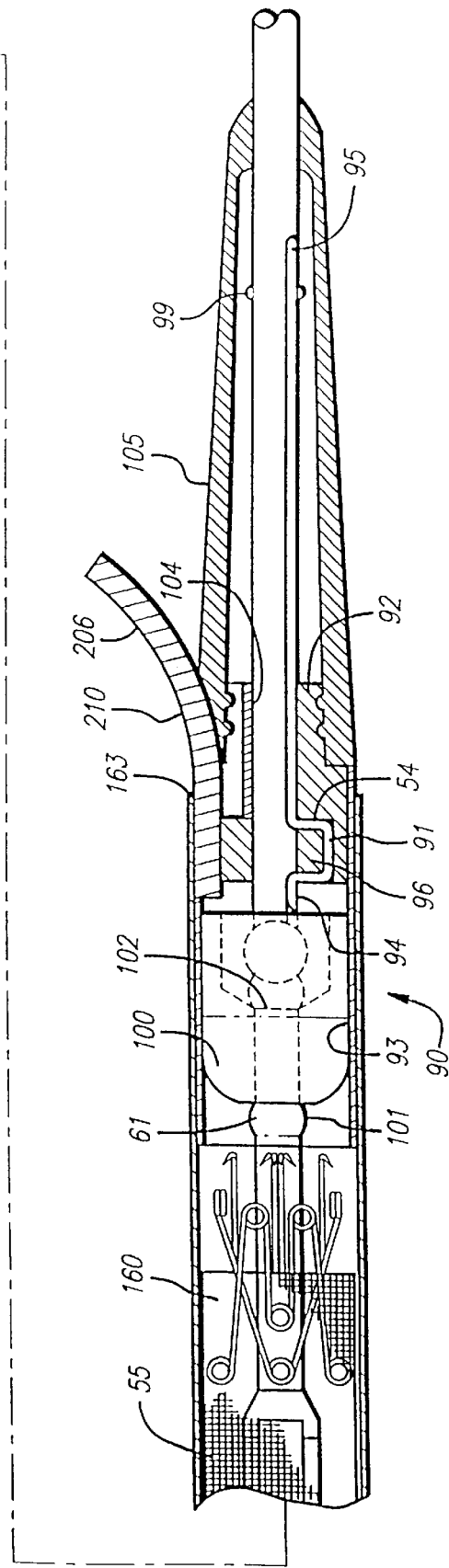
FIG. 8

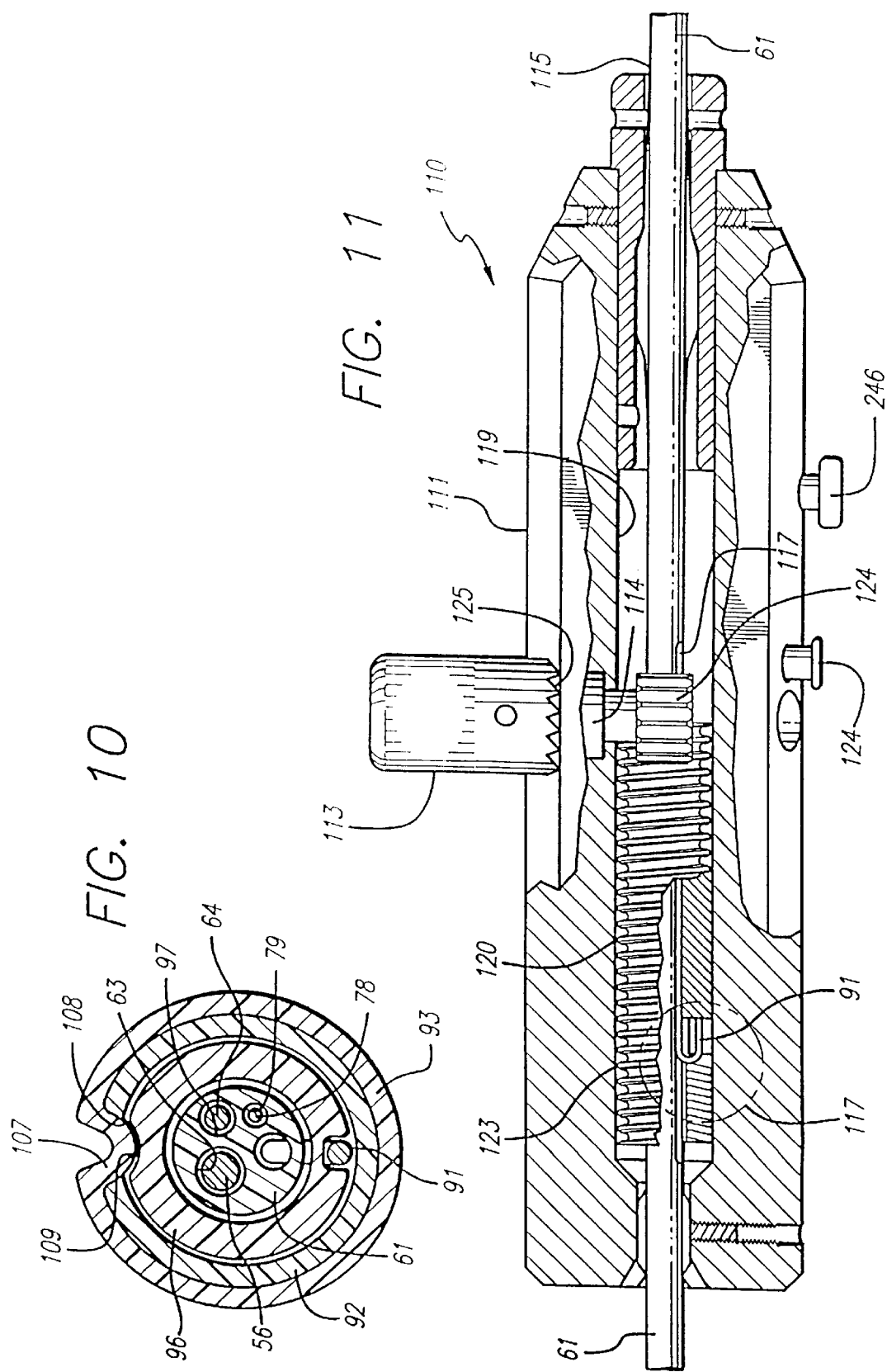

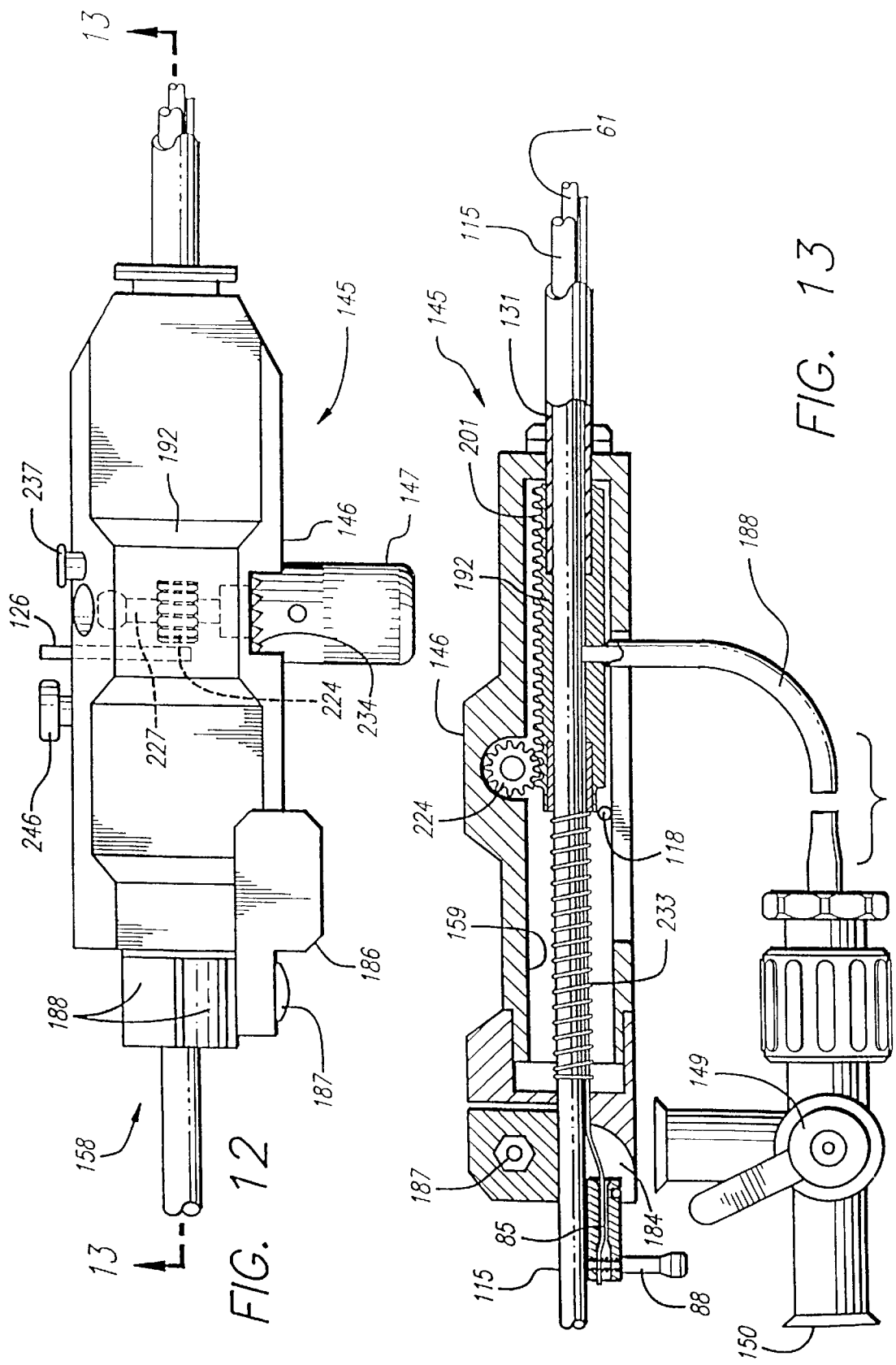

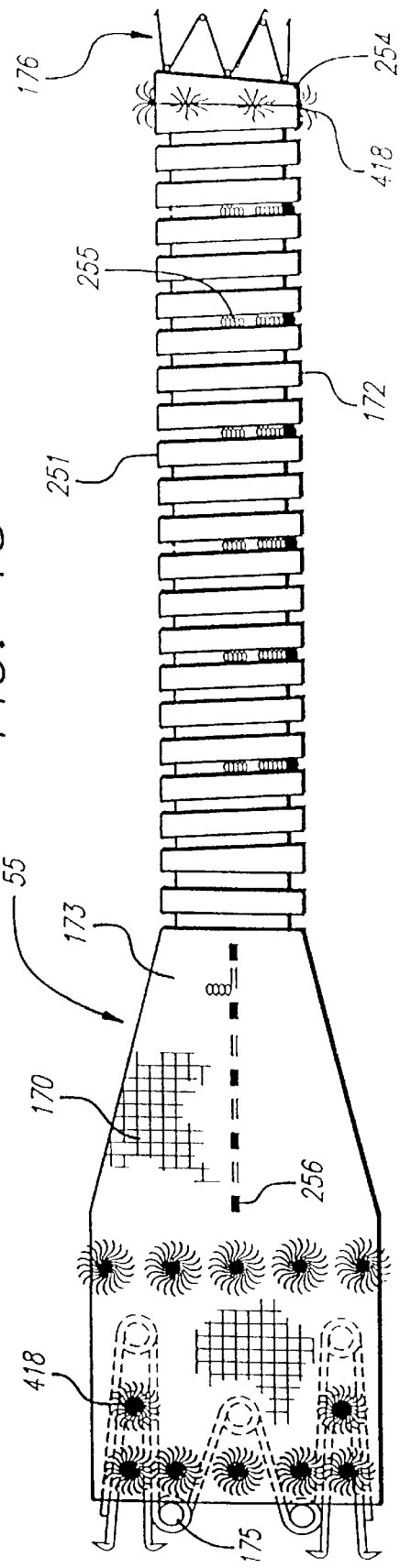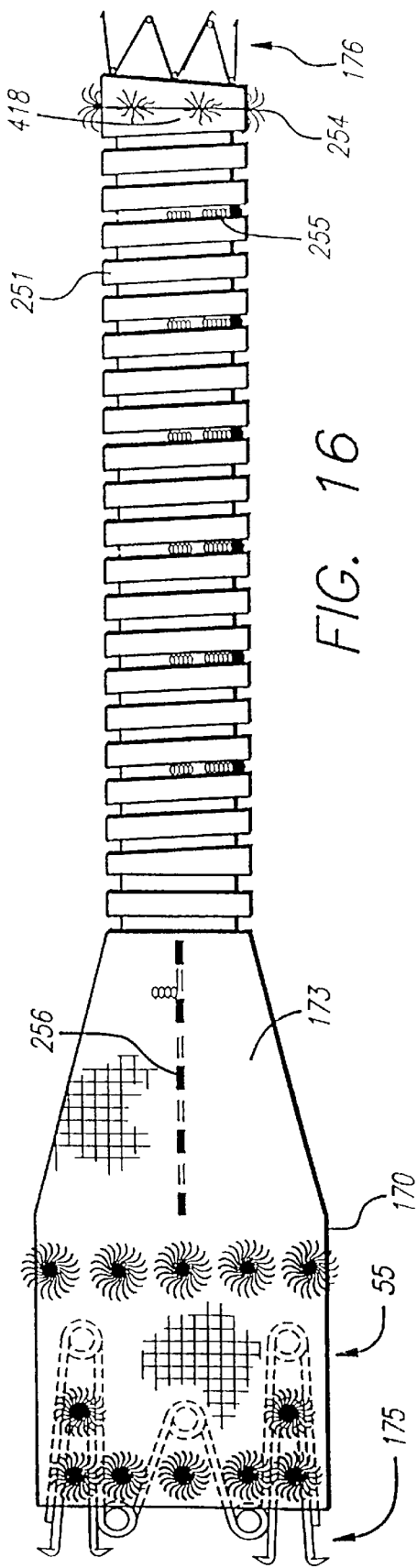

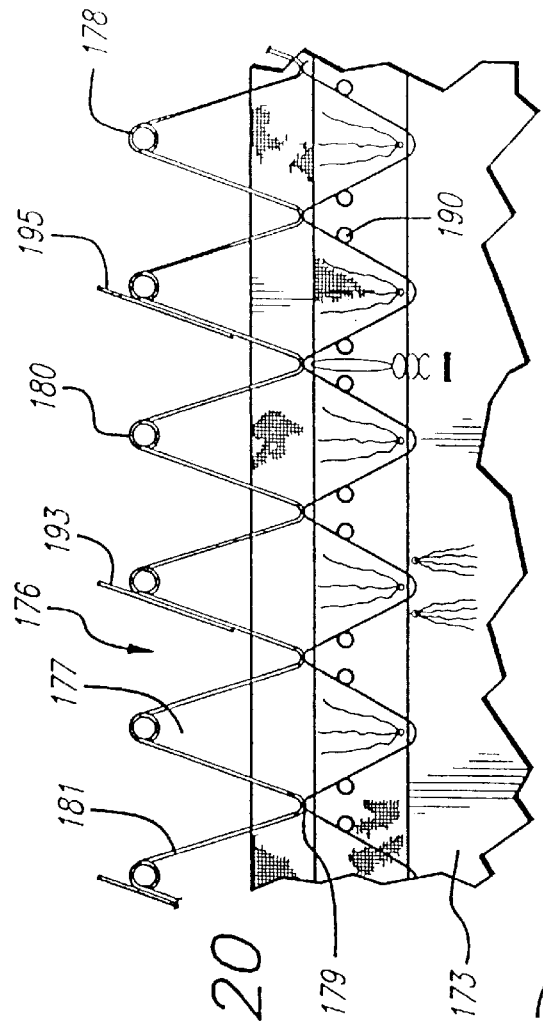
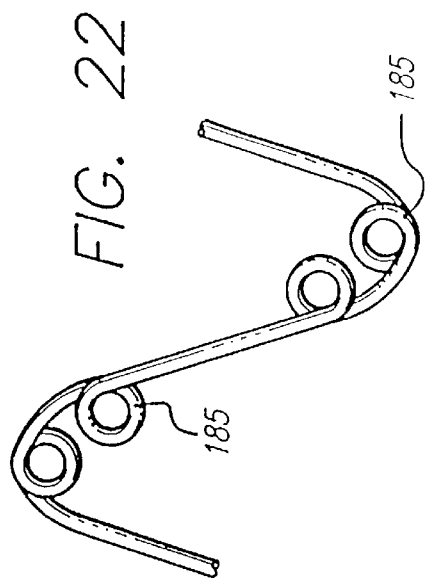
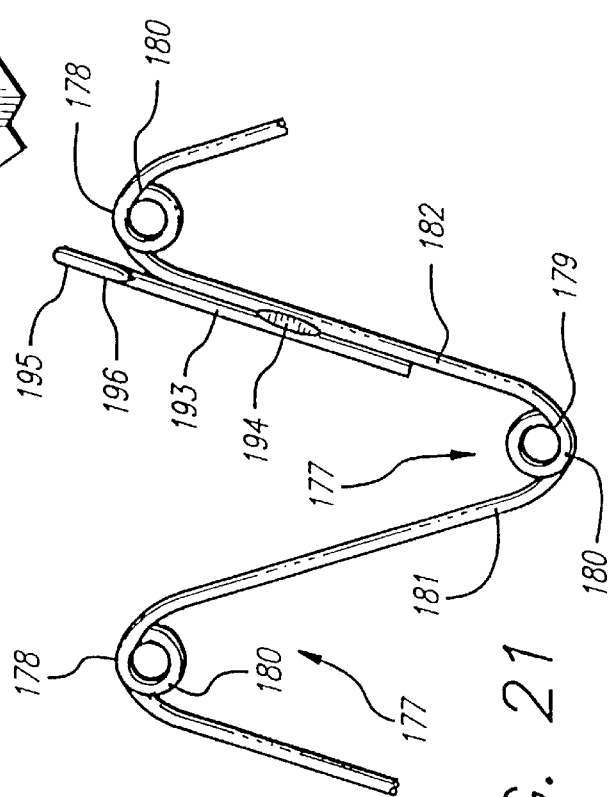
FIG. 20
FIG. 22
FIG. 21

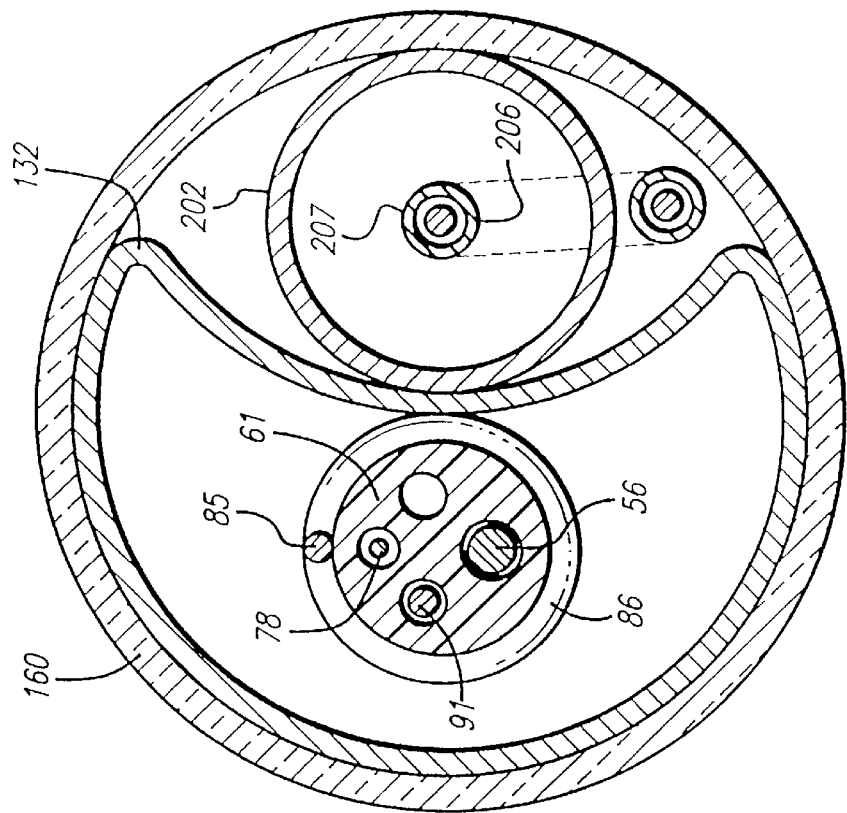
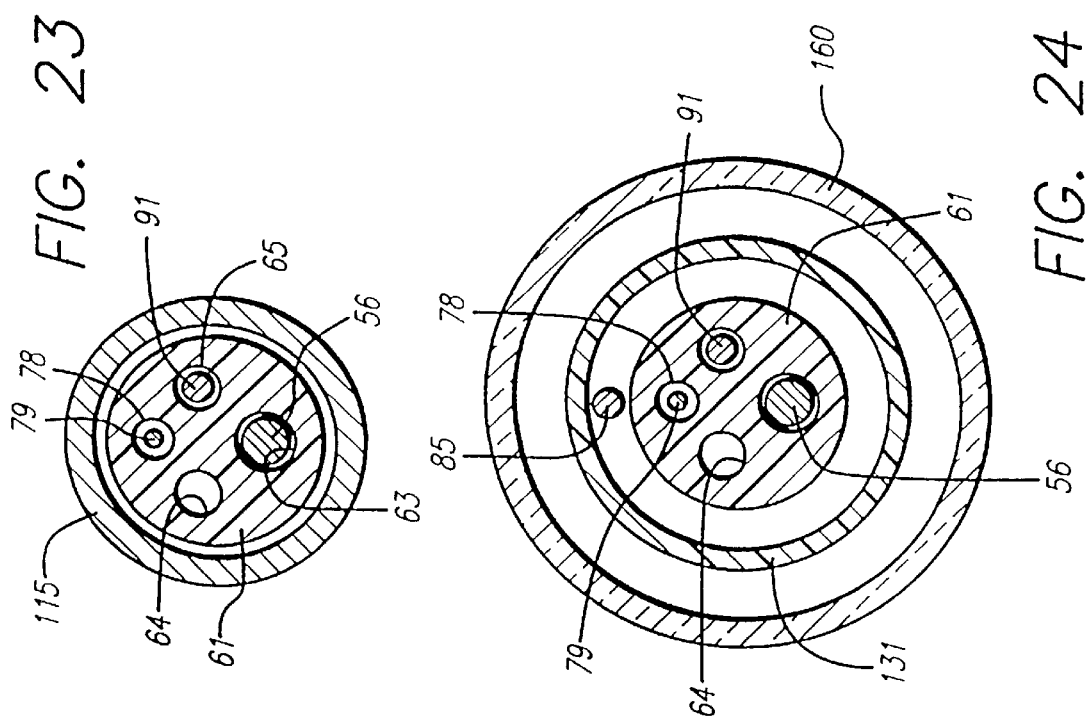

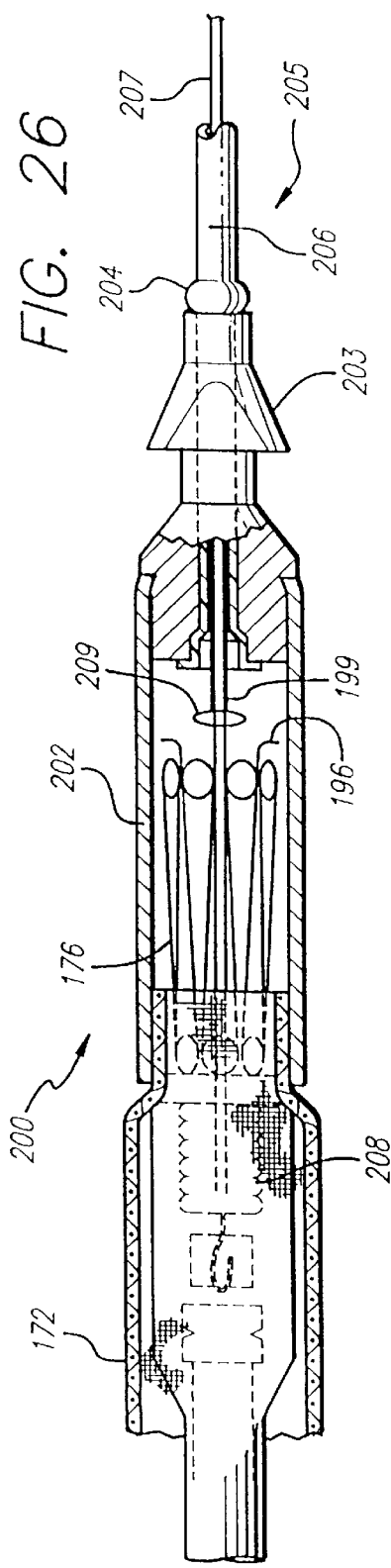
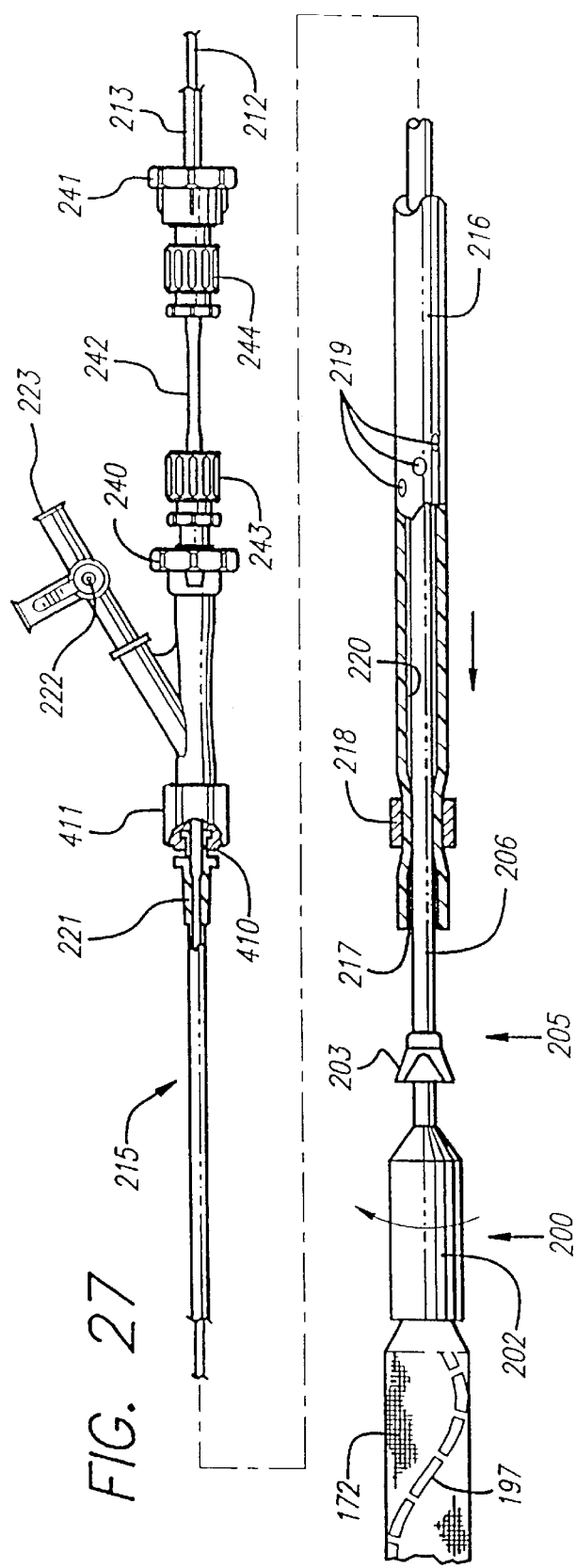
FIG. 26
FIG. 27

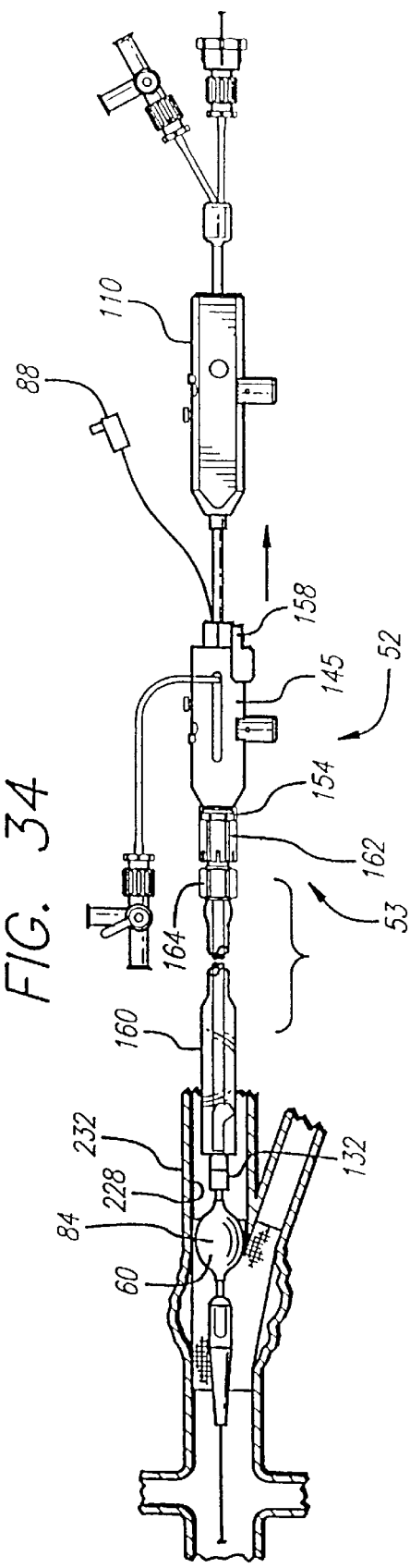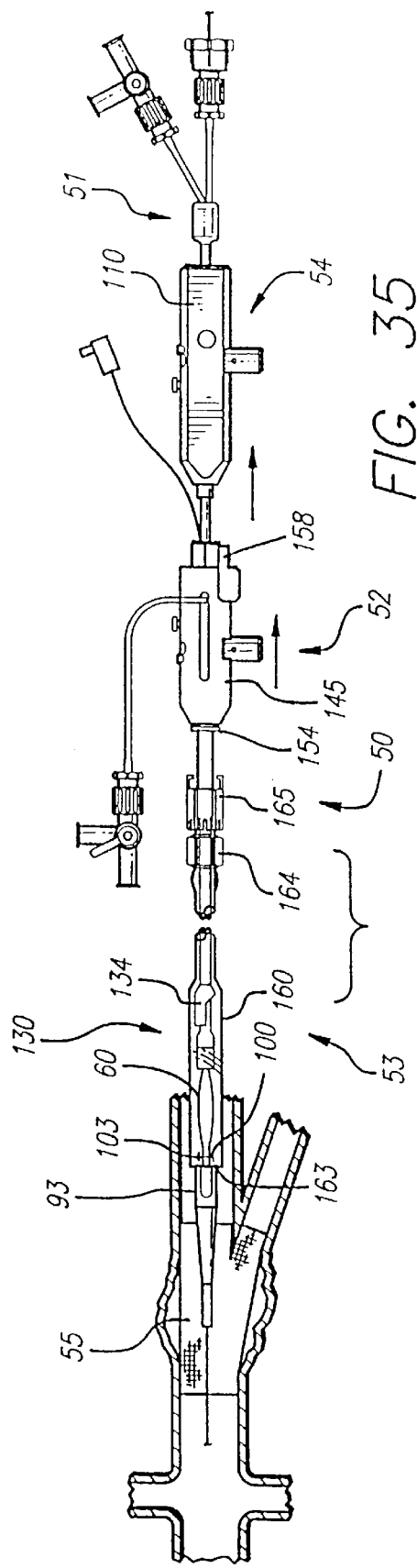

SYSTEM AND METHOD FOR
INTRALUMINALLY DEPLOYING A
BIFURCATED GRAFT

CROSS-REFERENCES TO RELATED
APPLICATIONS

This application is a continuation of application Ser. No. 08/996,330, filed Dec. 22, 1997, now U.S. Pat. No. 6,039, 758, which is a continuation of application Ser. No. 08/707, 179, filed Sep. 3, 1996 now U.S. Pat. No. 5,824,044, which is a continuation-in-part of application Ser. No. 08/241,476, filed May 12, 1994, now U.S. Pat. No. 5,628,783.

BACKGROUND OF THE INVENTION

This invention relates to an improved system and method for emplacing a prosthesis and, more particularly, to a delivery catheter and method of use for placement within a corporeal lumen of a bifurcated graft having attachment systems.

It is well established that various fluid conducting body or corporeal lumens, such as veins and arteries, may deteriorate or suffer trauma so that repair is necessary. For example, various types of aneurysms or other deteriorative diseases may affect the ability of the lumen to conduct fluids and in turn may be life-threatening. In some cases, the damaged lumen is repairable only with the use of prosthesis such as an artificial vessel or graft.

For repair of vital vessels such as the aorta, surgical repair is significantly life-threatening. Surgical techniques known in the art involve major surgery in which a graft resembling the natural vessel is spliced into the diseased or obstructed section of the natural vessel. Known procedures include surgically bypassing the damaged or diseased portion of the vessel and inserting an artificial or donor graft attached to the native vessel by an anastomosis.

It is also known within the art to provide a prosthesis for intraluminal repair of a vessel, such as an abdominal aorta having an aneurysm. The art has taught to provide a prosthesis positioned in a vessel then securing the prosthesis within the vessel with hooks or staples that are mechanically extended by the user. The early prior art devices were large in diameter, mechanically complex and in turn were susceptible to mechanical failure. Prior intraluminal grafting systems have embodied capsule catheters or balloon catheters, but were relatively stiff and of a relatively high profile. Similarly, the prior art systems were configured in such a way that the graft was relatively difficult to deploy in the correct position. In addition, prior systems having a capsule catheter assembly were usually configured such that the prosthesis was disposed within a unitary capsule. Further, the prior prostheses were sometimes ill suited to withstand the high pressures existing in the vessels and, consequently, experienced structural failures.

Generally speaking, intraluminal repair of vessels or body lumens, where it is a viable alternative, can be performed with less threat to a patient. Moreover, since intraluminal repair does not require major surgery, the recovery time from such a procedure is usually shorter. However, in order to fully take advantage of the benefits of an intraluminal repair procedure, the system for accomplishing the same must be optimized to efficiently and effectively place a prosthesis within the vessel or lumen. Furthermore, the prosthesis itself must be optimally configured so that it can withstand and adapt to the environment in which it is placed. Accordingly, there is a need for the system to be configured such that advancement and deployment of the prosthesis can be accomplished in an efficient manner and such that the prosthesis can be accurately placed so that the attempted repair is effective. Additionally, there is a need for a prosthesis which itself is specifically configured for the environment existing within the vessel or lumen in which it is placed. The present invention addresses these needs.

To provide consistency with the common usage of terms used in the medical surgical arts in the United States, the terms "proximal, distal, inferior and superior" are used with a certain regularity within the present specification. Proximal refers to parts of the system, such as catheters, capsules and wires, which are closest to the user and closest to the portion of the system outside or exterior of the patient. Distal refers to the point farthest from the user and typically most interior to the corporeal lumen. The term superior refers to a location situated above and is used herein in description of the graft and attachment system. Inferior refers to the point situated below and again is used herein with the graft and attachment system. Thus, for applications in the abdominal aorta which use a femoral approach, the superior end of the graft resides within the most distal portion of the delivery catheter. Likewise, the inferior end of the graft resides within the proximal capsule which is on the most distal portion of the capsule catheter.

The term "ipsilateral" typically refers to a vessel or part of a device which resides on the same side in which a device enters a lumen. For example, the ipsilateral tubular leg of a graft would be the tubular leg which resides in the iliac artery in which the capsule catheter enters the aorta. Similarly, the term "contralateral" refers to a vessel or device residing on the opposite side of which the main device enters the aorta. For example, the contralateral attachment system resides in the contralateral iliac artery which is on the opposite side of the aorta from which the capsule catheter enters the aorta.

SUMMARY OF THE INVENTION

Briefly, and in general terms, the present invention provides a new and improved intraluminal delivery system for securing a prosthesis within or between vessels or corporeal lumens of an animal, such as a human. The preferred embodiment of the placement system is configured for introducing a graft into a corporeal lumen and positioning the graft in the area of the aortic bifurcation.

Basically, the present invention is directed to a system and method for implanting a prosthesis or graft utilizing a catheter assembly having a multiplicity of capsules. The delivery system includes a guide wire, a balloon catheter assembly, a distal capsule assembly, an ipsilateral capsule catheter assembly, a contralateral capsule assembly, and a capsule jacket assembly. The system also includes control wire, locking wire and guiding tube assemblies. Also provided are a torque catheter and a stub nose balloon catheter.

The prosthesis comprises a wye shaped bifurcated graft having a self-expanding attachment system at each of its three orifices. Each attachment system is contained within its own compact capsule assembly during deployment. The capsule assemblies are movable relative to each other to allow the graft to be emplaced at the desired location in the corporeal lumen. The graft and capsules are deployed by a catheter assembly designed for traversing the femoral, iliac and aortic vessels of a human anatomy.

The present system has several advantages over prior art systems. In particular, the present system incorporates various novel structural features which enhance the efficiency of the system as well as facilitates the effective deployment of the prosthesis within a vessel or body lumen. Moreover, the present system embodies a design which is optimized for ease of operation and manufacturability. Additionally, the prosthesis includes various advancements which also enhance the overall effectiveness of the system.

More particularly, the ipsilateral capsule catheter assembly includes a handle embodying a rack and pinion device which is configured coaxially with the ipsilateral capsule catheter tubular member in order to provide precise control as well as includes a conveniently assessable collet lock for engaging the balloon catheter shaft. The capsule jacket assembly includes a capsule jacket having a more easily manufacturable one-piece design and in a preferred embodiment, it is constructed from LDPE material.

The new and improved distal or superior capsule assembly includes a superior end configured with a nose cone for improved maneuverability of the intraluminal delivery system within vessels or corporeal lumens, as well as for providing a gradual transition of the overall profile of the delivery system. The control wire assembly also includes a handle having a more manufacturable single piece design and embodies a rack and pinion device which is configured coaxially with the control wire for more precise control.

The lock wire assembly is provided with an ipsilateral lock spaced-apart from a pusher button which can be manipulated such that a limb of the prosthesis can be deployed in tension or compression. Also, the inferior end of the locking wire assembly includes a handle shaped so that it can be manipulated more conveniently. The pull wire assembly includes a slidable pusher button and a lock which cooperate in order to provide the system with the capability of deploying another prosthesis limb in tension or compression. The guiding tube assembly also includes additional marking bands for providing an enhanced view of the guiding tube assembly under fluoroscopy. The guiding tube assembly also includes non-radiopaque marker bands for conveniently identifying the chronological sequence in which portions of the guiding tube assembly are removed during the deployment process.

The torque catheter includes a detachable inferior extension to fully expose the superior end of the guiding tube assembly, which is necessary when deploying a prosthesis limb in compression or in tension. The superior end of the stub nose balloon catheter is configured so that it effectively engages the slidable pusher button.

The improved prosthesis includes additional radiopaque members positioned along its length for the purpose of better identifying the configuration of the prosthesis under fluoroscopy. The improved prothesis also includes additional means for insuring an enhanced ingrowth and sealing effect within the vessel or corporeal lumen. Furthermore, the superior end of the prosthesis is provided with a superior attachment system embodying V-shaped members with hooked terminal ends which cooperate with a generally sinusoided frame to seat the superior end of the prosthesis within a vessel or lumen. This improved attachment system is optimally configured to be effective even in harsh environments wherein significant stresses are placed upon the members comprising the attachment system. Significantly, the number of connecting points among the various members of the superior attachment have been minimized.

The new and improved procedure for manipulating the intraluminal delivery system to thereby deploy the prosthesis or graft within a vessel or lumen necessarily takes advantage of the various novel structural features incorporated into the delivery system. In particular, additional steps are contemplated to accomplish deploying the limbs of the prosthesis either in tension or compression. Moreover, additional steps are included to more optimally maintain a sterile operating field as well as ensure proper orientation of the prosthesis within the vessel or lumen.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1 is a side plan view of an intraluminal grafting apparatus and system incorporating the present invention.

FIG. 2 is a side plan view of a guide wire to be used with the endovascular grafting system of the present invention.

FIG. 3 is a side plan view of the balloon catheter and ipsilateral locking wire of the present invention.

FIG. 4 is a side plan view of the distal capsule, control wire, hypotube and control wire handle assembly of the present invention.

FIG. 5 is a side plan view of the proximal capsule and ipsilateral capsule catheter assembly of the present invention.

FIG. 6 is a side plan view of the capsule jacket assembly of the present invention.

FIG. 7 is a top plan view of a bifurcated graft and contralateral capsule assembly of the present invention.

FIG. 8 is a partial cross-sectional view of the distal end of the intraluminal grafting apparatus and system along the line 8—8 of FIG.1.

FIG. 10 is a cross-sectional view taken along the line 10—10 of FIG. 9.

FIG. 11 is a partial cross-sectional view of the control wire and control handle mechanism shown in FIG. 4.

FIG. 12 is an enlarged side perspective view of the ipsilateral capsule handle.

FIG. 13 is a cross-sectional view of FIG. 12 taken along line 13—13 of FIG. 12.

FIG. 15 is a contralateral side view of the bifurcated graft of FIG. 14.

FIG. 16 is an ipsilateral side view of the bifurcated graft of FIG. 14.

FIG. 20 is an top plan view showing a inferior attachment system as sewn into a tubular leg of the graft.

FIG. 21 is an enlarged side plan view showing an inferior attachment system.

FIG. 22 is an enlarged side plan view showing an attachment system having a supplemental helix torsion spring at the apices.

FIG. 23 is a cross-sectional view taken along the line 23—23 of FIG. 1.

FIG. 24 is a cross-sectional view taken along the line 24—24 of FIG. 1.

FIG. 25 is a cross-sectional view taken along the line 25—25 of FIG. 8.

FIG. 26 is a partial cross-sectional view of the contralateral tubular leg and attachment system positioned in the contralateral capsule assembly.

FIG. 27 is a top plan view of a torque catheter disposed over the guiding tube of the contralateral capsule assembly of the present invention.

FIG. 34 is a partial cross-sectional view of the intraluminal grafting system, wherein the inflatable member of the balloon catheter has been moved and inflated proximate the inferior attachment system of the ipsilateral tubular leg.

FIG. 35 is a partial cross-sectional view of the intraluminal grafting system, wherein the balloon catheter, capsule catheter and capsule jacket have been placed in a position for withdrawal from the corporeal lumen.

DESCRIPTION OF THE PREFERRED EMBODIMENTS

Figure 9:
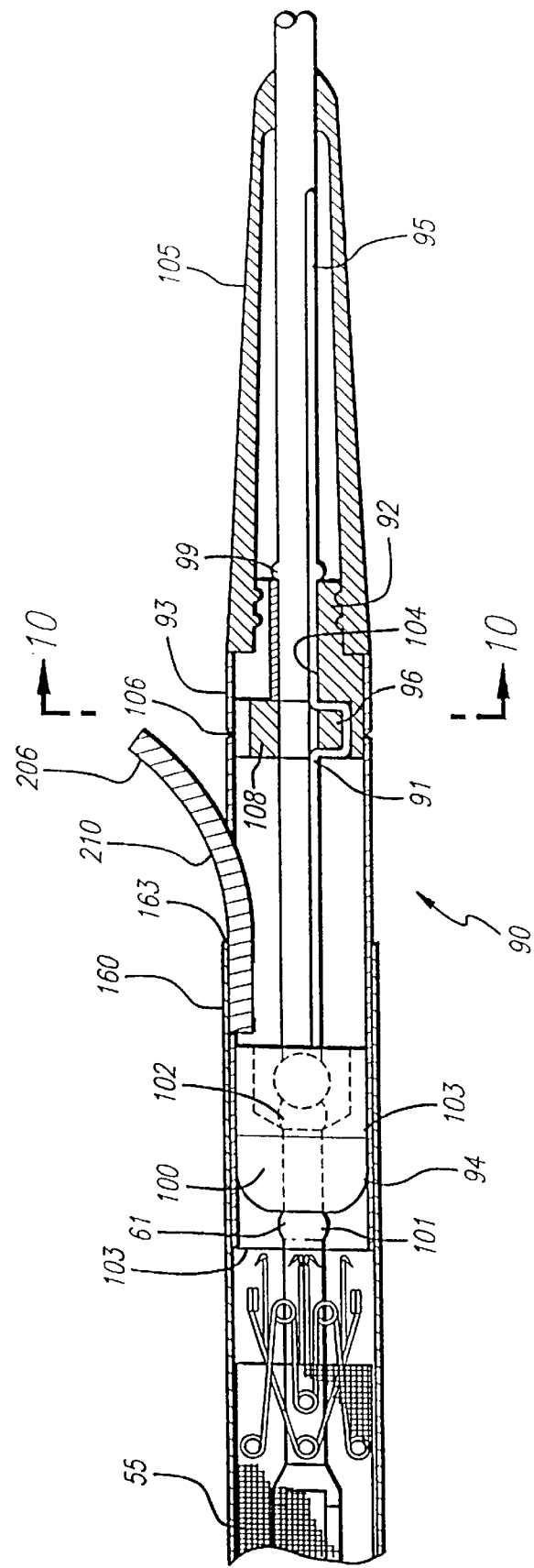
FIG. 9 is the partial cross-sectional view of FIG. 8, with the distal capsule and control wire moved proximally within the balloon catheter.

As shown in the drawings and for purposes of illustration, the invention is embodied in an intraluminal grafting system of the type having a balloon catheter assembly, an ipsilateral capsule catheter assembly, contralateral and distal capsule assemblies and means interacting therewith, and a protective sleeve or capsule jacket. The novel features of the present system are directed towards enhancing the efficiency of the intraluminal grafting system, facilitating the effective deployment of a prosthesis within a vessel or body lumen and providing a prosthesis well suited for effectively repairing the vessel or lumen.

In the present system, the prosthesis or graft is comprised of a bifurcated tubular body having superior and inferior extremities. The superior extremity of the graft comprises a main tubular member which bifurcates into two tubular legs which comprise the inferior extremity of the graft. For clarity, the two tubular legs are referred to herein as the ipsilateral tubular leg and the contralateral tubular leg. An attachment system is secured to the superior end of the main tubular member as well as to the inferior ends of each of the tubular legs. Each attachment system is provided with lumen piercing members which are covered during deployment by the proximal/ipsilateral, distal and contralateral capsule assemblies. The balloon catheter, capsule catheter and capsule jacket are configured coaxially so that relative movement between them provides for deployment of the graft. The inflatable member of the balloon catheter is used to firmly implant the attachment systems, and thereby the graft, in the lumen.

In more detail, the intraluminal grafting system 50 is shown in FIGS. 1–8. The system includes a balloon catheter assembly 51, which is coaxially disposed within ipsilateral capsule catheter assembly 52, which is coaxially disposed within capsule jacket assembly 53. As shown in FIG. 8, the ipsilateral or proximal capsule assembly 130, contralateral capsule assembly 200 and distal capsule assembly 90 are used to contain the bifurcated graft 55. A control wire assembly 54 is coaxially disposed within a lumen of the balloon catheter assembly and configured to move the distal capsule assembly in relation to the other system components. In the preferred embodiment, the system is used as an over-the-wire device, such that the balloon catheter is further configured with a lumen for a guide wire 56. It is contemplated, however, that the system can also be used with well known fixed wire delivery system configurations.

As shown in FIGS. 1 and 3, the intraluminal grafting system 50 also includes a balloon catheter assembly 51 which consists of an inflatable member or balloon 60 secured to a flexible elongate element or balloon catheter shaft 61. As shown in FIG. 23, the balloon catheter shaft is preferably configured with four lumens; however, the balloon catheter may be configured with a single, dual or triple, or similar multilumen shaft. A guide wire lumen 63 extends the length of the balloon catheter shaft. Similarly, a balloon inflation lumen 64 extends from the proximal end 70 of the balloon catheter to the inflatable member 60, wherein an inflation port (not shown), is provided to allow inflation fluid to enter and exit the inflatable member. The third lumen 65 is provided for a control wire 91. A fourth lumen 78 is provided for an anti-elongation reinforcement wire 79 made from kevlar fiber or equivalent material. In the preferred embodiment, the reinforcement wire 79 extends the length of the balloon catheter shaft.

The flexible elongate element or balloon catheter shaft 61 is preferably formed of a material suitable for intraluminal use, such as irradiated polyethylene tubing. The four lumen balloon catheter shaft is preferably extruded to an outside diameter of 0.08 inches (2.03 mm). The guide wire lumen 63 has an inner diameter of 0.042 inches (1.07 mm). The inflation lumen 64 and the control wire lumen 65 have identical inner diameters of 0.022 inches (0.56 mm). The reinforcement wire lumen 78 is 0.009 inches. However, the lumen inside diameter may range from 0.006 to 0.06 inches (0.381–1.52 mm) and the outside diameter may range from 0.035 to 0.1 inches (0.889–2.54 mm) for a multilumen balloon catheter shaft. The balloon catheter may vary in length to suit the application, for example, from fifty to one hundred-fifty centimeters.

Referring to FIG. 1, the proximal extremity 70 of the balloon catheter shaft 61 is secured to a splitting adapter 71 which splits the guide wire lumen 63 from inflation lumen 64. The side arm 72 of the adapter 71 has a stop cock 73 mounted at its proximal end which is movable between open and closed positions. The stop cock is provided with a Luer fitting 74 which is adapted to be secured to a syringe for injecting inflation fluid. The side arm 75 of the splitting adapter 71 is connected to female Luer fitting 77 for distal tip injection and to a Touhy Borst adapter 76 which is configured to removably and slidably receive the guide wire 56. The reinforcement wire 79 is disposed and attached in the reinforcement wire lumen 78 between the splitting adapter and the control handle assembly 110 at the proximal end, and at its distal end near the distal extremity 80 of the balloon catheter shaft 61.

The inflatable member or balloon 60 is preferably secured twelve centimeters from the distal extremity 80 of the balloon catheter shaft 61. The balloon is positioned proximal of the distal capsule assembly 90 and the superior end of the graft 55. For shorter grafts of four to seven centimeters in length, the inflatable member may be positioned distal of the distal capsule assembly. The balloon is formed of suitable material such as polyethylene. The polyethylene utilized for the balloon is irradiated to achieve an appropriate balloon size. For larger diameter balloons, higher tensile strength materials like polyethylene-terephthalate (PET) is desirable because thinner walls, hence a lower profile, can be achieved.

The balloon can vary in diameter from twelve to forty-five millimeters in diameter and can have a wall thickness ranging from 0.001 to 0.005 inches (0.0254–0.127 mm). The preferred balloon made in accordance with the present invention has an outside diameter of 20 to 26 millimeters, a diameter equal to the inner diameter of the graft, and has a wall thickness of approximately 0.003 inches (0.076 mm). The range may be 18 to 28 millimeters. In addition, the balloon is pleated along its axis for a low profile which facilitates its introduction into a corporeal lumen of a patient as hereinafter described. Further, the deflated balloon is heated to provide it with a memory of its low profile configuration.

The balloon catheter shaft 61 is provided with an inflation lumen 64 which is in fluid communication with the balloon 60. The inflation lumen is used to inflate and deflate the balloon 60 by introducing and withdrawing a gas or liquid through the inflation port. The balloon proximal stem 81 and balloon distal stem 82 are heat sealed to the balloon catheter shaft to form a fluid tight seal. The length of the proximal stem may vary from 0.5 to 1.0 centimeter.

A radiopaque marker 84 is embedded in the balloon catheter shaft approximately two millimeters distal the balloon inflation port. The radiopaque marker is a platinum or tungsten coil one centimeter long with an outer diameter of 0.02 inches (0.508 mm) and is located proximate the center of the balloon 60. Preferably two radiopaque platinum marker bands, 8 millimeters apart, with an outer diameter of 0.080 are positioned over the balloon catheter shaft 61 and are located proximate the center of the balloon 60. A strain relief or support wire may be disposed in the inflation lumen 64 between the distal end 80 of the balloon catheter shaft and the balloon distal stem 82 if a three lumen balloon catheter is used.

It should be appreciated that although a separate inflatable member has been described, an integral coaxial inflatable member may be provided which is formed of the same tubing from which the balloon catheter shaft is made. This can be readily accomplished, as is well known to those skilled in the art, by using an additional radiation dose for the balloon region of the shaft.

The balloon 60 can also be observed under x-rays if carbon dioxide is used as the inflation medium, because the blood in the patient's vessel is more opaque than the gas used for inflating the balloon. In addition, increased visibility of the balloon can be obtained by inflating the balloon with a diluted radiopaque contrast solution. Moreover, radiopaque bands of a suitable material such as platinum, gold or a platinum-tungsten alloy can be placed on the proximal and distal balloon stems 81 and 82 to aid in ascertaining the position of the balloon. Similarly, radiopaque rods may be inserted in the balloon inflation lumen.

As shown in FIGS. 1, 3 and 8, the ipsilateral locking wire 85 runs parallel to the balloon catheter 61 within the ipsilateral capsule catheter assembly 52. The distal end of the ipsilateral locking wire may be configured with a proximal pusher button 86 and a distal/ipsilateral lock button 87 secured approximately twelve millimeters apart. The radiopaque buttons are oblong shaped and include thru-holes 89 which slideably receive balloon catheter shaft 61. The buttons are disposed within the distal end of the ipsilateral capsule catheter assembly during deployment and secure the ipsilateral attachment system of the bifurcated graft 55 within the distal end of the capsule catheter assembly.

The proximal end of the ipsilateral locking wire 85 extends through the proximal end of the ipsilateral capsule catheter assembly 52. The proximal extremity of the locking wire is specially configured with a handle 88 which is configured for gripping. The ipsilateral locking wire handle is used to laterally move the radiopaque proximal button 86 and distal pusher lock 87 which engage the ipsilateral attachment system of the ipsilateral tubular leg of the bifurcated graft 55. Rotation of the knob 113 (see FIG. 4) permits retraction of the proximal/ipsilateral capsule to expose the ipsilateral attachment system which is held fixed relative to the cororeal lumen via the ipsilateral lock 87 and pusher button 86. Movement of the ipsilateral locking wire handle in relation to the ipsilateral capsule catheter assembly permits removal of the ipsilateral lock and pusher button back into the capsule catheter assembly after the deployment of the ipsilateral attachment system. Preferably, the pusher button will be twice as long as the lock to allow full deployment of the ipsilateral attachment system while keeping the pusher button partially contained in the ipsilateral capsule.

The intraluminal grafting apparatus also includes a control wire assembly 54, which is shown in FIGS. 1 and 4. The distal end of the control wire assembly consists of a distal capsule assembly 90. As shown in more detail in FIGS. 8–10, the distal capsule assembly comprises a control wire 91 disposed within a distal cap 92 and distal cap spacer 96 disposed within the distal cap. The distal cap spacer is secured to the distal cap by means of an adhesive, solvent bonding, ultrasonic welding or by heat shrinking. A hollow distal capsule 93 is secured to the distal cap and coaxially surrounds the control wire and balloon catheter shaft 61. The superior end of the distal cap is secured to nose cone 105 which provides the delivery system with improved maneuverability through vasculature due to its gradually tapered profile. Preferably, the nose cone 106 is formed of a low durometer plastic material such as polyester block amide under the trademark "PEBAX" with Bismuth Subcarbonate or barinon sulfate for radiopacity.

The control wire 91 is slidably disposed in the control wire lumen 65. A longitudinal slot 94 is cut out of the balloon catheter shaft 61 to expose the control wire lumen and the control wire. To secure the control wire within the distal capsule assembly 90, the control wire is configured between the distal cap 92 and the distal cap spacer 96. The control wire is formed in a U-shaped bend over the distal cap spacer and is configured to slide within the slot and the control wire lumen of the balloon catheter shaft. The distal end 95 of the control wire resides in the portion of the control wire lumen beyond the distal end of the slot.

The configuration shown in FIGS. 8–10 allows the distal cap assembly to move axially along the balloon catheter shaft. The U-shaped bend of the control wire over the distal cap spacer 96, however, prevents the distal cap assembly from rotating in relation to the balloon catheter shaft. As described above, the distal cap spacer is firmly secured within the distal cap 92. To prevent rotation of the distal cap, a three centimeter length of the control wire extends distal of the distal cap and is slidably disposed in the control wire lumen 65 of the balloon catheter shaft 61.

As shown in FIG. 8, bullet 100 is secured to the balloon catheter shaft 61 at a position distal the balloon distal stem 82 and proximal the aperture 94. The bullet is secured to the balloon catheter shaft by means of two retaining bumps 101 and 102 and alternatively in conjunction with adhesive. These retaining bumps secure the bullet in place, limiting its movement. Such a configuration provides a rounded, atraumatic transition from edge 103 of the distal capsule 93 resting on the top surface of the bullet when the distal capsule is its most distal position as shown in FIG. 9.

As the control wire 91 is moved in a longitudinal manner, the distal end 95 of the control wire, the distal cap spacer 96, the distal cap 92, the distal capsule 93 and the nose cone 105 each move as a single assembly. The proximal edge 103 of the distal capsule is rolled, curved or crimped inward, or deburred and smoothened so that the proximal cap will provide a smooth transition along the distal capsule assembly 90 when the distal capsule is advanced. The distal movement of the distal capsule is limited by a third retaining bump 99 positioned approximately 2.5 centimeters distal the distal cap 92. The third retaining bump limits the amount of distal movement of the distal capsule assembly so that when the assembly is fully advanced the proximal edge of the distal capsule coincides with the top surface of the proximal cap 100.

The distal cap 92 may be formed from polycarbonate or other suitable material for insertion through the body lumen. Similarly, the distal cap spacer 96 and nose cone 105 may be formed of the same material as the distal cap. The distal cap spacer and distal cap provide a bore 104 for receiving the balloon catheter shaft. The distal cap is further provided with a recess 106 or other means for receiving the distal end of the distal capsule 93. The distal capsule is preferably formed of stainless steel, but may be formed of other suitable biocompatible material, such as a nickel titanium. The distal cap recess 106 is angled to allow crimping of the distal capsule 93 to the distal cap 92. In addition, the distal capsule is configured with a longitudinal semicircular recess 107 in which the guiding tube 206 resides during device insertion. Similarly, the distal cap is configured with a cutout slot 108 and the nose cone 105 is configured with a longitudinal recess 109 to accept the recess in the distal capsule. The distal cap cutout inhibits the relative rotation between the bullet 100 and ultimately the balloon capsule shaft 61.

The outside diameter of the distal cap 92 and capsule 93 may range from 4 to 9 millimeters and is preferably 0.282 inches (7.16 mm) in outer diameter and 0.276 inches (7.01 mm) inner diameter. Similarly, the bullet 100 is comprised of stainless steel and has an outside diameter slightly less that of the distal capsule so as to provide a smooth transition. The proximal end of the proximal cap is preferably rounded to minimize trauma in the vessel and to facilitate balloon retraction into the bifurcated graft 55 during the emplacement process. In an alternate embodiment, the proximal cap may have a tapered profile. The distal capsule may range in length from one to five centimeters, and preferably is 3.5 centimeters long so as to adequately retain the superior extremity of the main tubular member of the graft. The nose cone 105 may range from 1 to 5 centimeters and preferably is 3.8 centimeters long.

As shown in FIGS. 1 and 11, a handle assembly 110 is secured to the proximal end of the control wire 91. The handle assembly comprises a body 111, a control knob 113 with rotating shaft 114 and a hypotube 115. For ease of manufacturability and simplicity of design, the handle body has a one-piece design. Also, the body has a central bore 119 for receiving the balloon catheter shaft 61 as well as a retaining screw 118 for longitudinally locking the retaining rack relative to the handle.

The hypotube 115 is coaxially disposed over the balloon catheter shaft 61 and extends distally from the central bore 119 in the handle body 111. The proximal end of the hypotube is secured to the balloon catheter shaft by means of a polyethylene sealing tube 116 which is heat shrunk over the proximal end of the hypotube. An adhesive may be used to fix the distal handle body to the hypotube.

Hypotube 115 consists of a rigid thin wall tube formed of a suitable material such as stainless steel. The hypotube has a length of about 55 centimeters and has an outside diameter of 0.095 inches (2.41 mm) and an inside diameter of 0.087 inches (2.21 mm). When a crimped graft 55 is used, the hypotube may have marker bands (not shown) at predetermined positions distal of the control handle body 112. A crimped graft is loaded into the capsule assemblies in its most stretched configuration. After the capsule jacket assembly 53 is retracted, then adjustments need to be made to the position of the hypotube relative to the capsule catheter assembly 52 for the graft to resume its crimped length under physiological pressure. The marker bands facilitate the correct positioning of the inferior end of the graft.

The control wire 91 (see FIGS. 4, 23) resides in a balloon catheter lumen 65 and extends from the distal capsule assembly 90 to an aperture 117 located in the lumen just proximal of the proximal end of the hypotube 115. The control wire preferably consists of an elongate solid flexible stainless steel wire having a lubricating coating, such as fluorinated ethylene-propylene (FEP). The coated control wire is about 0.02 inches (0.508 mm) in diameter, providing sufficient strength to move the distal capsule assembly without buckling or kinking.

The proximal end of the control wire 91 is secured to a retaining rack 120, which is approximately 4.5 centimeters long. The retaining rack is slidably disposed within the central bore in the handle 111 and is in coaxial alignment with the balloon catheter shaft 61 and control wire 91. This coaxial design provides precise control of the relative movement of the control wire (including the components attached thereto), and remaining portions of the intraluminal grafting system 50.

The retaining rack 120 is configured with teeth 123 along a longitudinal edge which engage a pinion or gear 124. The pinion is attached to a lower end of the rotating shaft 114. The upper end of the rotating shaft is secured within the control knob 113 such that rotation of the control knob rotates the gear and in turn moves the retaining rack, including the components attached thereto, longitudinally within the central bore 119. Longitudinal movement of the retaining rack causes longitudinal movement of the proximal end of the control wire 91, causing like longitudinal movement of the distal end 95 of the control wire and of the distal capsule 93 (including the components attached thereto).

The base of the control knob 113 is configured with a locking gear 125 which has angled teeth. The angled teeth engage a locking pin 126 which can be biased by a locking spring (not shown). The configuration of the curved teeth allows the control knob to turn in only one direction while the locking pin engages the locking gear. When the locking pin is removed from engagement with the locking gear 125, then the control knob may be turned in either direction. The locking gear is preferably molded as part of a plastic control knob, but may be a separate mechanism secured to the base of the control knob.

As shown in FIGS. 1, 5, 12 and 13, the ipsilateral capsule catheter assembly 52 consists of a proximal (ipsilateral) capsule catheter assembly 130 secured to the distal end of a flexible elongate tubular member 131 formed of a suitable plastic material such as polyether block amide available under the trademark "PEBAX", available from Atochem Polymers, Glen Rock, N.J. The capsule catheter elongate tubular member is of a suitable length as, for example, forty to one hundred centimeters and preferably approximately seventy-five centimeters for the abdominal aortic-iliac arteries and approximately ninety-five centimeters for the thoracic aortic artery. The elongate tubular member has a preferred outside diameter of 0.187 inches (4.75 mm) and an inside diameter of 0.125 inches (3.175 mm). The elongate tubular member can be produced in a certain color such as blue. Preferably, the elongate tubular member can be extruded with braided wire to improve torsional response. To render the elongate tubular member radiopaque under x-rays, its material of construction may contain a radiopaque material, such as twenty percent by weight of bismuth subcarbonate or barium sulfate. The elongate tubular member may have markings or bands distal of the handle 145 at predetermined positions to indicate capsule jacket retraction and locking points.

The proximal catheter assembly 130 includes a proximal (ipsilateral) capsule 132 mounted on the distal extremity of the ipsilateral capsule catheter elongate tubular member 131. The elongate tubular member also serves as a shaft for advancing the proximal capsule, as hereinafter described. Thus, the elongate tubular member should have a diameter which is less than that of the proximal capsule, preferably having an outside diameter ranging from three to seven millimeters.

The proximal capsule 132 is configured to approximately match the size of the distal capsule assembly 90. The proximal capsule is somewhat oval in shape, having opposite concave and convex outer surfaces, resembling a crescent moon (FIG. 25). The proximal capsule has a preferred diameter ranging from four to nine millimeters, which may be configured to accommodate different size grafts. The proximal capsule is preferably made of stainless steel or similar impermeable and rigid, or semi-flexible material.

Referring to FIG. 8, the proximal (ipsilateral) capsule 132 is secured to the distal extremity of the elongate tubular member 131 by means of a capsule adapter assembly 133. The capsule adapter assembly comprises a housing 134, which may be constructed from polycarbonate. The capsule adapter housing distal extremity 136 is secured in the proximal extremity of the capsule, for example, by crimping, by using a press fit swaging or an adhesive such as a cyanoacrylate ester. The capsule adapter housing distal extremity may be angled to facilitate securing the housing to the proximal capsule.

The proximal extremity of the capsule adapter housing 134 is secured to the distal extremity of the elongate tubular member 131 by means of an cyanoacrylate ester adhesive, or other suitable means. To facilitate a mechanical lock, the elongate tubular member distal extremity is molded to form a flange 137, wherein the capsule adapter housing is configured so as to mate with the flange. Preferably, the capsule adapter is of polycarbonate material insert molded to the distal extremity of the elongate tubular member 131.

An ipsilateral capsule handle 145 is secured to the proximal extremity of the elongate tubular member 131 of the ipsilateral capsule catheter assembly 52. The ipsilateral capsule handle comprises, for ease of manufacturing and simplicity in design, a one-piece body 146, a control knob 147 with rotating shaft 148 and a collet lock assembly 158 which tightens around the hypotube 115 disposed in a central bore 159 of the handle. The central bore 159 also receives the elongate tubular member 131 of the capsule catheter assembly. A stop cock 149 is mounted on the tubular member 188 extending from retaining rack 192 within the one-piece body 146 and being in fluid communication with the elongate tubular member 131 therein which is movable between open and closed positions. The stop cock is provided with a Luer fitting 150 which is configured to accept a syringe for injecting a dye or other fluid.

Air may be purged from the capsule jacket assembly 53 by injecting fluid through the Luer fitting 150. The injection fluid and air will exit purge ports 151 and 152, thereby filling the capsule jacket assembly with injection fluid. The Luer fitting also may be attached to a saline drip line during the operative procedure and may be used for contrast hand syringe injections for real time angiograms.

The ipsilateral locking wire 85 is disposed in the ipsilateral capsule catheter assembly 52 through a slotted opening 184 in the collet lock assembly 158. The collet lock assembly includes a rotating arm 186, shaft 187 and opposing members 188. The slotted opening is formed in one of the two opposing members. Additionally, opposing members provide a throughway for the balloon catheter shaft 61 contained within hydrotube 115. Upon activation of rotating arm 186, the balloon catheter shaft can be locked and unlocked via the hypotube 115.

Slideably disposed within central bore 159 is a retaining rack 192 which is in coaxial alignment with elongate tubular member 131. Also disposed within the central bore is a spring 233 which operates to bias the retaining rack distally and to support the ipsilateral lock wire when subjected to compressive loads during the deployment of the ipsilateral attachment system preventing wire buckling, kinking or bowing. The proximal end of the elongate tubular member is secured to the retaining rack. The coaxial design of the rack and elongate tubular member provides precise control of the relative movement of the elongate tubular member, the components attached thereto, and the remaining portions of the intraluminal grafting system 50. The retaining rack is configured with teeth 201 along a longitudinal edge which engage a pinion or gear 224 fix to the lower end of a shaft 227. The upper end of the shaft is secured to control knob 147 such that rotation of the central knob rotates the gear and in turn moves the retaining rack longitudinally within the central bore. Longitudinal movement of the rack causes longitudinal movement of the elongate tubular member and of the capsule 132 (including the components attached thereto). The control knob is configured with a locking gear 234 which has angled teeth for releasably engaging a locking pin 237. The locking pin can be biased by a locking spring (not shown).

Referring to FIGS. 1, 6 and 8, the capsule jacket assembly 53 is slidably disposed coaxially over the ipsilateral capsule catheter assembly 52 and the balloon catheter assembly 51 (FIG. 24). The capsule jacket assembly is comprised of a main sheath 160, a locking connector 162 and a locking ring/adapter 164. The sheath has a one piece design for ease of manufacturability and simplicity in design and is preferably made from HOPE or equivalent material such as LDPE, FEP, PET. At the distal extremity of the sheath, it flares to a larger diameter covering the proximal (ipsilateral) capsule 132, the contralateral capsule 202, the bifurcated graft 55 and the distal capsule 93. The diameter of the main sheath is about 0.263 inches (6.68 mm) at its proximal end and about 0.3 inches (7.62 mm) at the distal end 163.

The proximal end of the sheath 160 is secured to the ring/adapter 164 and locking connector 162 by mechanical means and by adhesive. In addition, a length of polyethylene tubing 167 is adhered over the sheath adapter and over the proximal ends of the sheath to secure the parts from separating. The distal end of the sheath of the capsule jacket is provided with radiopaque marker 166 about five millimeters in longitudinal length. The preferred embodiment is an "L" shaped marker of 3 mm LEG×5 mm LEG×2 mm WIDTH gold radiopaque foil laminated 2 mm from the distal extremity 163 of capsule jacket assembly 53.

When the capsule jacket assembly 53 is in its most distal position, the distal end 163 of the capsule jacket main sheath 160 extends to cover at least a portion of the distal capsule assembly 90. Similarly, the capsule jacket locking connector 162 is thereby positioned just proximal the proximal capsule catheter purge port 151. Prior to insertion into the lumen, the locking ring/adapter 164 is turned down to hold the capsule jacket assembly firmly in place, thereby maintaining a smooth transition surface along the length of the intraluminal grafting system 50. When the locking ring/adapter is released, the capsule jacket assembly may be moved to a furthermost proximal position, wherein at least a portion of the proximal capsule catheter assembly is exposed. At its furthermost proximal position, the locking connector is positioned adjacent the distal of the ipsilateral capsule handle 145. The distal end of the ipsilateral capsule handle is configured with a male component 154 and mates with the proximal end of the locking connector. The locking ring/adapter may be tightened at any intermediate position to firmly secure the capsule jacket assembly at the desired location. In addition, a radiopaque marker 166 is provided at the distal end of the main sheath to facilitate proper linear positioning of the main sheath.

Figure 14:
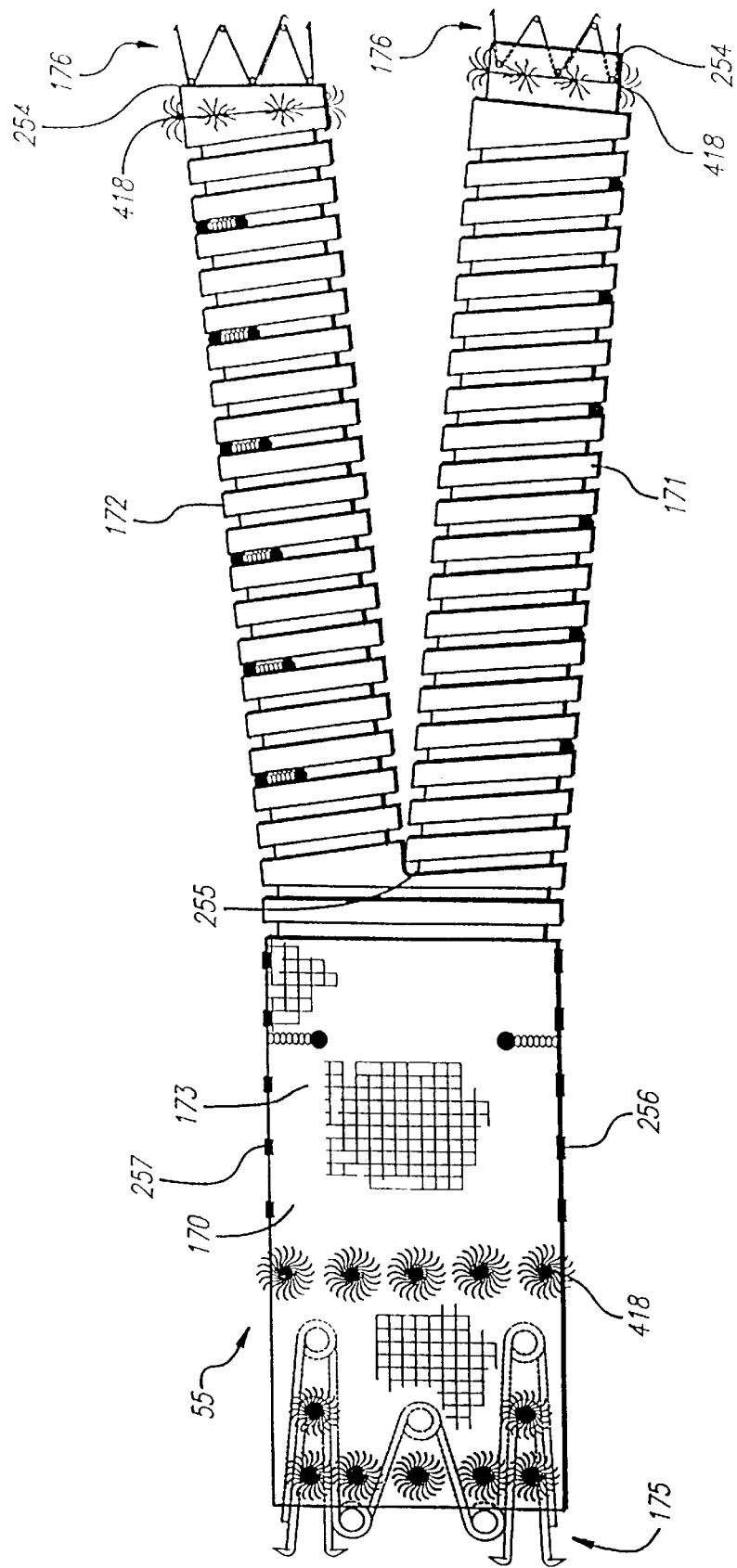
FIG. 14 is an enlarged top plan view of a bifurcated graft of the present invention having crimped tubular legs.

As shown in FIGS. 1, 7 and 14–16, the intraluminal grafting apparatus 50 also includes an expandable, collapsible and flexible intraluminal vascular bifurcated prosthesis or graft 55 for implanting in a body vessel or corporeal lumen. Referring to FIG. 14, the graft consists of a deformable main tubular member 170 which bifurcates into an ipsilateral tubular leg 171 and a contralateral tubular leg 172. The main tubular member and tubular legs each are formed of a substantially cylindrical or continuous wall 173 allowing fluid communication between the superior and inferior ends of the bifurcated graft.

The main tubular member 170 may have a length in the range of two to ten centimeters, where 6.5 centimeters is suitable for most patients. The main tubular member may have a maximum expandable diameter ranging from fourteen to forty millimeters and a minimum diameter in a collapsed condition of 0.175 to 0.3 inches (4.44–7.62 mm). The tubular legs 171 and 172 may have a length in the range of three to ten centimeters, where five centimeters is suitable for most patients. The graft wall 173 can be woven of any surgical implantable material such as polytetrafluroethylene or a polyester fiber made from polyethylene terephthalate (PET), such as "DACRON" (Type 56). One material found to be satisfactory is "DEBAKEY" soft woven "DACRON" vascular prosthesis (uncrimped) sold by C. R. Bard of Billerica, Mass. In order to prevent unraveling of the woven material at the ends, the ends can be melted with heat to provide a small melted bead of material on each end. Alternatively, the prosthesis may be of PTFE material, knitted polyester or any surgical implantable material.

As shown in FIGS. 14–17, crimps 251 are configured in the ipsilateral and contralateral tubular legs 171, 172 to resist kinking of the graft when deployed in a corporeal lumen. However, it is to be recognized that, where crimping is not desired, they can be omitted from the structure of the graft. The crimps begin just superior to the bifurcation from the main tubular member 170 and are evenly spaced along the tubular leg. The crimps discontinue approximately 7 (seven) millimeters superior the inferior ends 254 of the tubular legs so as to provide sufficient space for the inferior attachment systems (not shown) to be sewn into the inferior ends of the tubular legs. The crimps may be annularly or helically spaced along the tubular leg. Similarly, crimps may also be provided in the main tubular member of the graft.

Although a standard size crimp may be used, it is preferred to make the crimps 251 radially deeper and less numerous than produced from standard crimping techniques. Having sparsely crimped tubular legs 171, 172 reduces the elongation properties of the bifurcated graft 55. Also, a sparsely crimped graft is easier to pack into the capsule jacket than a standard crimped graft. The low bulk and low elongation of the crimped graft further allows that the inferior ends of the graft may be packed into smaller diameter capsules. Similarly, the low crimp elongation factor allows for a higher degree of placement accuracy in conjunction with marker bands on the hypotube of the balloon catheter to adjust for the in-vivo length of the crimped graft which is the graft length with the crimps subjected to physiologic pressures in the corporeal lumen.

Whereas the standard crimp have peak widths of about two times the graft wall thickness, the crimps 251 of the bifurcated graft 55 may be of sufficient width, preferably 1.5 millimeters, so as to sew in radiopaque markers 255 in the valleys between selected crimps. Alternatively, the radiopaque markers can be sewn on the face of selected crimps. The radiopaque markers are preferably 5 mm long platinum coils sewn on the outerseam of the tubular legs in a crosswise orientation that appear "C" shaped, allowing for twist detection under fluoroscopy. Similarly, long radiopaque markers 256 and short radiopaque markers 257 are secured to the edge of the main tubular member 170 to ensure proper alignment of the graft 55 in line with the outseam of the tubular legs and aligned with the markers on the tubular legs. Also, in the preferred embodiment, one or more radiopaque markers are secured to the graft at the point of bifurcation.

The distance between the crimps 251, or crimp pitch, is preferably less than the diameter of the tubular legs 171, 172, so as to resist kinking. The crimp pitch is preferably 3.25 millimeters. The crimped graft 55 of the present invention is configured with crimps having peaks that are preferably one millimeter deep. So configured, the graft will maintain its high flexibility even under arterial pressures of over one hundred mm Hg within the corporeal lumen.

Referring to FIGS. 14–19, a self-expanding superior attachment system 175 is secured adjacent the superior end of the tubular member 170. As shown in FIGS. 14–16 and 20, a first self-expanding inferior attachment system 176 is secured adjacent the inferior end of the ipsilateral tubular leg 171. Similarly, a second self-expanding inferior attachment system 176 is secured adjacent the inferior end of the contralateral tubular leg 172. Each attachment system serves to yieldably urge the graft 55 from a first compressed or collapsed position to a second expanded position and provides a fluid tight seal between the graft and corporeal lumen wall.

Figure 17:
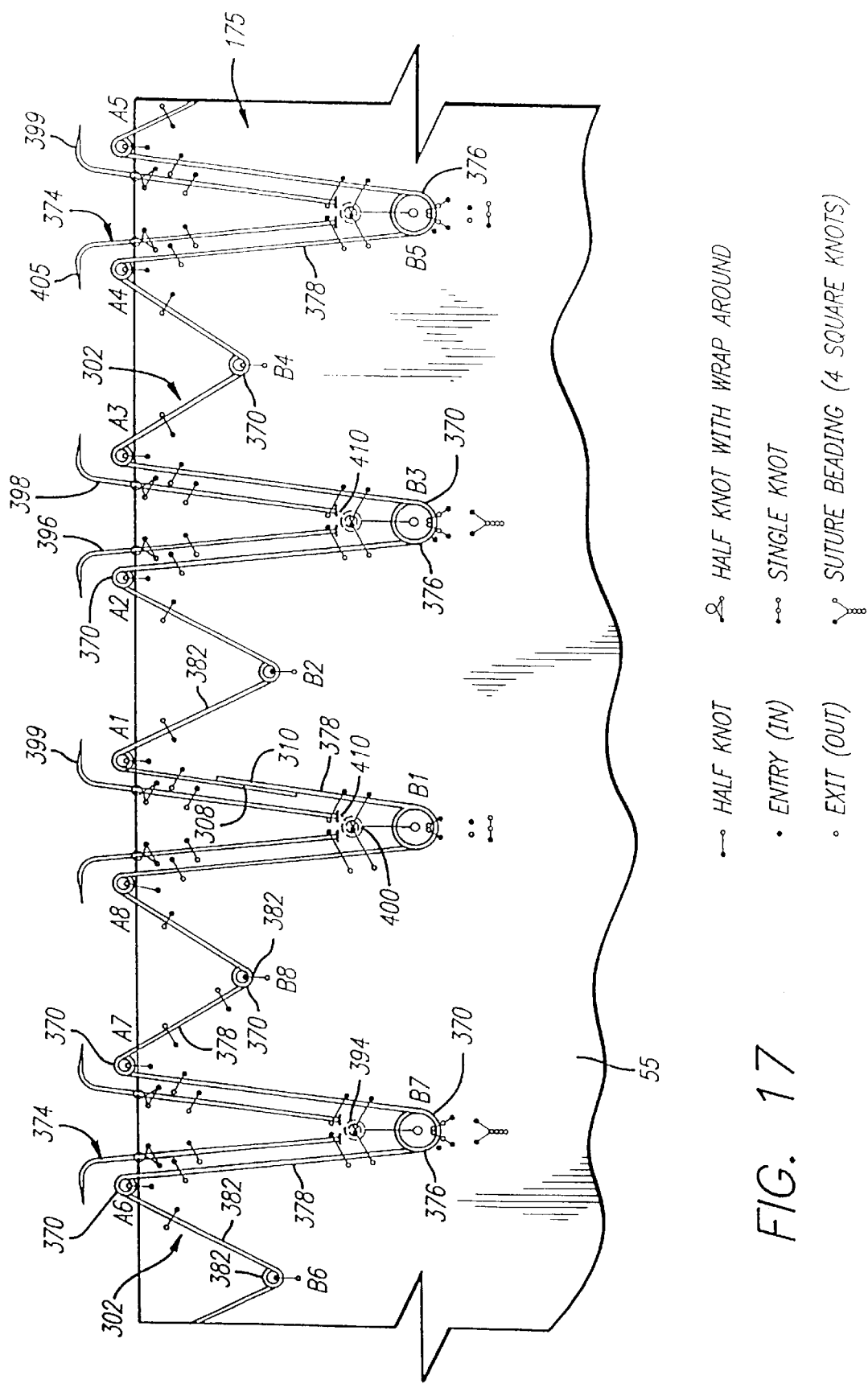
FIG. 17 is a plan view of the inside of the graft cut longitudinally, showing a superior attachment system as sewn into the main tubular member of the graft.
Figure 18:
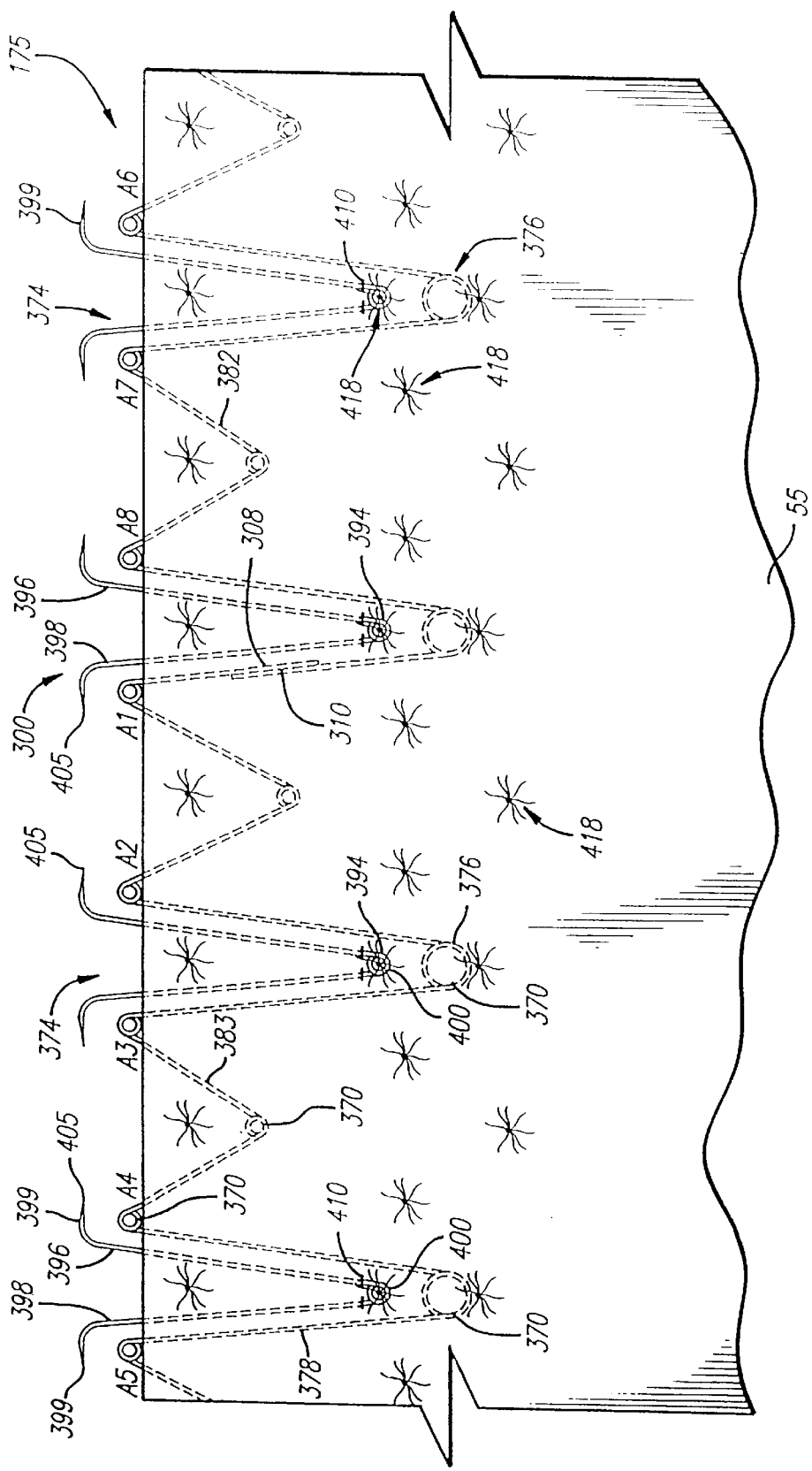
FIG. 18 is a plan view of the outside of the graft cut longitudinally, showing in partial hidden view the wire frame and separate lumen engaging members and further showing the tufts attached to the graft.
Figure 19:
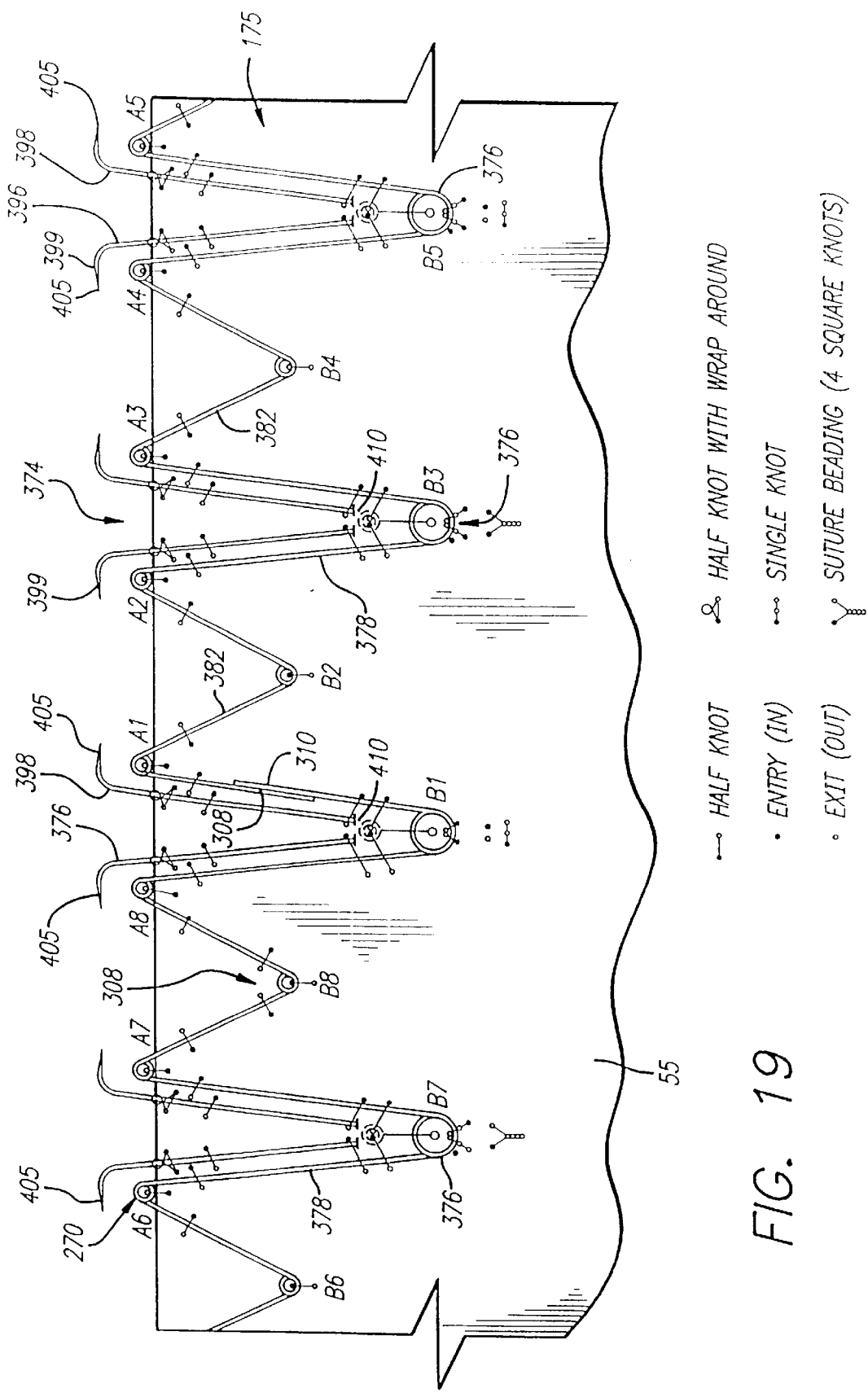
FIG. 19 is a plan view of the inside of the graft cut longitudinally, showing an alternative embodiment of the wire frame, lumen penetrating members and stitching of the attachment system.

As shown in FIGS. 17–19, the superior attachment system 175 includes a sinusoidal frame 302 that has longitudinally inwardly directed base apices that are affixed to the graft longitudinally inward from the outer extremity. Alternatively spaced between the sinusoidal frame are outwardly directed protruding apices that extend outward from the end of the graft. As shown in the embodiment illustrated in FIG. 17, the wire frame has a first end strut 308 and a second end strut 310. In the prefered embodiment, the first and second end struts of the single piece of wire frame are welded together to provide a continuous spring like attachment system. The wire frame is wound into helical coils or helices with one and a half rotations and include apices A1 through A8.

In the prefered embodiment, the sinusoidal wire frame 302 is formed with eight outward protruding apices numbered A1 through A8 respectively beginning at the protruding apex A1 closest to the first end. Each of the apices are wound into a helical spring coil 370. The alternating base apices are numbered for reference B1 through B8 beginning with the base apices closest to apex A1.

Each of the protruding apices A1 through A8 are integrally connected to adjacent base apices B1 through B8 by struts 378. As observed in FIG. 17, not all of the struts are of equal length. Rather, the length of the struts are configured to stagger the apices along different planes that are spaced longitudinally apart and are perpendicular to the axis of the graft 55 according to the pattern described below. It is an important objective of the present invention to create a narrow profile for the attachment system 175 when the attachment system is constricted radially. Since the helical apices tend to have a greater radial width than the struts, staggering the apices serves the purpose of creating a narrow profile for insertion into a capsule. The helixes 370 located at outward protruding apices A1 through A8 are aligned slightly outward from the end of the graft. Furthermore, the diameter of the helices 370 at apice A1 through A8 are 0.042" inches which is smaller in diameter than helices 376 and 382. This accomplishes the purpose of minimizing the radial profile of the graft in collapsed position. The graft provides considerable bulk to the attachment system 175 and positioning the apices A1 through A8 beyond the end of the graft distributes longitudinally the bulk of the graft and helices.

The helixes 370 located at the base apices B1 through B8 are staggered considerably. Apices B1, B3, B5, and B7 are configured with slightly larger diameter helices 376 to accommodate the lumen piercing members 374 which are bent into the shape of a vee. V-shaped lumen piercing members 374 will fit between the struts 378 adjacent to apices B1, B3, B5 and B7 in a close proximal relationship. The lengthened struts that connect the apices are sufficiently long to orient the apices B1, B3, B5 and B7 0.550" inches longitudinally inward from the protruding apices. Furthermore, the diameter of the enlarged helices 376 at apices B1, B3, B5, B7 are 0.050 inches (1.2 mm), which is considerably larger than the diameter of remaining smaller helices 382 formed in the wire frame 302. The smaller helices 382 have a diameter of 0.047 inches (1.1 mm) at apices B2, B4, B6 and B8. The enlarged helices 376, in combination with the lengthened struts 378, create a space between the struts 378 that extend longitudinally outward from the enlarged helices 376 formed in apices B1, B3, B5 and B7 that conform in shape to the V-shaped lumen piercing members 374 such that the lumen piercing members can fit into the attachment system in close proximity to the lengthened struts and the enlarged helices, without contacting or rubbing against the same.

As shown in FIG. 18 apices B2 and B6 may be further staggered with respect to apices B4 and B8. Apices B2 and B6 are oriented 0.46 inches longitudinally inward from the protruding apices. Apices B4 and B8 are oriented 0.36 inches longitudinally inward from the protruding apices.

As shown in FIG. 19, it may not be necessary or desirable under some circumstances to stagger apices B2 and B6 relative to B4 and B8. For example, the profile of the protruding apices A1 through A8 of the attachment system 175 might be sufficiently large that even if the staggering of helices B2 and B6 relative to B4 and B8 occurred it would not serve to reduce the diameter of the overall capsule. When staggering apices B2 and B6 relative to B4 and B8 would not serve to facilitate the use of a narrower capsule or delivery system, then aligning such apices may be desired.

The wire frame 302 of the attachment system 175 illustrated in FIGS. 17 through 19 is designed to fit inside a graft 55 that has a diameter of 20 to 26 millimeters but may range from 18 to 28 mm. When affixing the frame to the tubular graft, the wire frame is preferably partially compressed to maintain a constant outward bias against the wall of the graft. The two ends of the wire frame, 308 and 310, overlap and are welded to each other.

The attachment system 175 including the wire frame 302 and the V-shaped lumen piercing members 374 are sutured to the graft 55 at various points throughout the graft. The sewing pattern can best be viewed with reference to FIGS. 17 or 19 showing the stitching from the perspective of the inside of the graft.

In the embodiment illustrated in of FIGS. 14, 17–19, the V-shaped lumen piercing members 374 are not welded to the wire frame 302, but rather are sewn into the graft 55 in close proximity to the sinusoidal wire frame and are responsive to the compression and expansion of the wire frame. To provide stability and flexibility, the lumen piercing members are formed from a single strand of wire with two ends. The wire is bent into a V-shape having an apex 394 and two outwardly protruding arms 396 and 398 that form an acute angle when in relaxed position. The two ends of the wire are bent radially outward to form hooks 399 that, when mounted to the graft, are designed to pierce into the wall of the blood vessel. As shown in FIGS. 18–20, the hooks are shown to point tangential to the graft perimeter. These illustrations are merely to show what the hooks look like. In actuality, the hooks would be directed at an angle perpendicular to the paper. At such an angle, the hooks would be difficult to illustrate. By incorporating this weldless design, the superior attachment system is better suited to withstand the pressures applied thereto when placed within a body lumen such as an aorta. There are no welds which, under repeated compression and expansion cycles, become fatigued and/or eventually break, thereby resulting in failures. Accordingly, being better suited for the environment in which it is placed allows the attachment system to more effectively anchor the graft within the lumen.

Each hook forms an angle with its respective arm ranging from ninety degrees to forty five degrees, but preferably seventy (70) degrees. The wire of each V-shaped lumen piercing member is wound at the apex to form a helical coil 400. Such a helical coil contributes to the outward bias and spring of the entire attachment system. Absent such a design feature, the V-shaped lumen piercing members would not be as responsive to the contractions of the graft. Moreover, the fatigue life of the hooks are extended because the helical design distributes the tension of the wire over the helix when the arms of the lumen piercing member are subject to continual contractions caused by the pulsing of the blood vessel during the cardiac cycle. The diameter of the apices in the embodiment illustrated in FIGS. 17, 18 and 19 should have an outside diameter ranging between 0.025 inches and 0.060 inches and preferably 0.047 inches.

There are four pairs of V-shaped lumen piercing members 374 in the embodiment illustrated in FIGS. 17, 18 and 19. The number of V-shaped lumen piercing members mounted depends upon the number of pairs of protruding apices and base apices. The V-shaped lumen piercing members are placed around the graft equally spaced apart. They are fitted into the space between the elongated struts 378 and are mounted adjacent to apices B1, B3, B5, and B7. The arms of the V-shaped lumen piercing members extend parallel to adjacent elongated struts. The V-shaped lumen piercing members of the embodiment illustrated in FIG. 17 has a length of 13.5 mm and a helical diameter of 0.047 inches but may range from 10–20 mm.

The hooks 399 have a length of two to three millimeters and are sharpened at the tips 405. The hooks may be sharpened with a conical tip as shown in FIGS. 17 through 19 or with a duck billed tip (not shown). A conical tip is formed when the wire tip is held at an angle against the sharpening tool (not shown) and rotated. The duck bill tip is formed by holding one side of the tip of the hook 399 against the sharpening surface (not shown) at an angle. Not rotating the wire results in an oblong flat surface and a sharpened curved cutting edge that cuts into the blood vessel wall when the hook is pressed against the vessel wall.

One possible method of attaching the V-shaped lumen piercing members 374 to the frame can be observed with reference to FIGS. 17, 18 and 19. As can readily be observed, the helices of the V-shaped lumen piercing members are located on the outside of the graft 55 while the arms 396 and 398 extend parallel to the struts along the inside of the graft 55. The frame is positioned within the interior of the graft wall apexes A1–A8 extending just beyond the end of the graft. By mounting the V-shaped lumen piercing members directly through the fabric of the graft, the V-shaped lumen piercing members will be mounted more firmly. Furthermore, the fabric of the graft separates the helix 400 of the V-shaped lumen piercing member from the respective adjacent enlarged helices 376 and thereby prevents the helices of the V-shaped lumen piercing member from rubbing against the adjacent base helices.

The V-shaped lumen piercing members 374 are mounted into the graft by pressing together the two arms 396 and 398 of the V-shaped lumen piercing members until the hooks are separated by a distance approximately equal to the outer diameter of the helices. The hooks are then punctured through the fibers of the graft from the outside of the graft wall to the inside of the graft. The entry holes made by the V-shaped lumen piercing members are spaced longitudinally outward by more than the outer diameter of the helices 400 of the V-shaped lumen piercing members. The spacing apart of helices 400 of the V-shaped lumen piercing members prevents them from radially overlapping the enlarged base helices 376. This longitudinal spacing also furthers the goal of distributing the bulk of the attachment system thereby narrowing the radial profile of the graft when in a compressed state. The apices of the lumen piercing member, prior to insertion of the hooks through the graft, point outward towards the end of the graft. The two hooks should preferably be laterally aligned so that the entry holes 410 through the graft wall created by the hooks are laterally aligned. The V-shaped lumen piercing members are pressed through the puncture holes and slid inward along the arms until the helix 400 contacts the outer wall of the graft. The V-shaped lumen piercing members are inverted to an upright position thereby orienting the hooks radially outward to engage the wall of the blood vessel.

The arms 396, 398 of the V-shaped lumen piercing members 374 are compressed before being sewn to the graft 55 to maintain the outward bias of the graft. The distance between the arms at the edge of the graft is preferably four to six millimeters but may range from 3–8 millimeters. The arms are sutured to the graft parallel to and in close proximal relationship to the struts 378 adjacent to the V-shaped lumen piercing members. The arms of the V-shaped lumen piercing members are generally not sutured directly to the adjacent struts. The arms of the V-shaped lumen piercing members and the adjacent struts are sutured separately in order to prevent them from rubbing together.

Referring to FIGS. 14–16 and 20, the inferior attachment systems 176 are formed of a plurality of vees 177 with the outer apices 178 and inner apices 179 of the vees being formed with helical torsion springs 180. The inferior attachment systems may be comprised of apices numbering from four to twenty-four. The springs yieldably urge the legs of each of the vees outwardly at a direction approximately at right angles to the plane in which each of the vees lie. The inferior attachment system 176 has legs 181, each being of equal length.

As shown in more detail in FIG. 20, the inferior attachment systems 176 are comprised of a single piece of wire which is formed to provide the vees 177 and also to define the helical torsion springs 180 between the legs 181. The two ends of the single piece of wire can be welded together to provide a continuous spring-like attachment system. In the construction shown in FIGS. 14 and 21, it can be seen that the attachment systems have twelve apices lying in two longitudinally spaced-apart parallel planes which are spaced with respect to the longitudinal axis of the tubular legs 171, 172. Accordingly, the outer apices 178 residing external of the graft are spread-apart from the inner apices 179 residing within the graft lie in the same plane. The apices, however, can lie in three or four spaced-apart planes if the inner and outer apices are staggered.

As can also be seen, each of inferior attachment systems includes three wall engaging members 193 which are welded to the legs, and spaced uniformly about the attachment systems.

With respect to the ipsilateral leg of the graft 55, the attachment system 176 may be sewn to the graft such that the inner apices 179 are positioned 2.5–3 centimeters within the interior of the graft. As to the contralateral legs 172, the inner apices 179 may be attached to the end of the leg. The inferior attachment systems 176 are secured to the wall 173 of the graft 55 by suitable means such as a polyester suture material. As shown in FIG. 20, sutures or knots 190 are used for sewing the inner apices 179 onto the wall of each tubular leg 171 and 172.

As shown in FIG. 21, wall engaging members 193 are preferably secured to the legs 181 of the attachment systems 176 in the vicinity of the outer apices 178 by suitable means such as a weld 194. The wall engaging members have a diameter ranging from 0.007 to 0.018 inches (0.254–0.457 mm) and a length from 0.5 to 5.0 millimeters. The wall engaging members are preferably sharpened to provide conical tips 196, and should have a length which is sufficient for the tip to penetrate into and perhaps through the corporeal lumen wall. The wall engaging members of the inferior attachment system 176 are configured in a similar manner. In the preferred embodiment, in order to provide additional structural support to the wall engaging members, the suture material used to sew the attachment system to the graft is wrapped around the legs of the attachment system to which the wall engaging members are welded, through the adjacent apices and is anchored to the graft.

The attachment system 175, inferior attachment systems 176 and the wall engaging members 193, 374 are formed of a corrosion resistant material which has good spring and fatigue characteristics. One such material found to be particularly satisfactory is "ELGILOY" which is a cobalt-chromium-nickel alloy manufactured and sold by Elgiloy of Elgin, Ill. The wire can have a diameter ranging from 0.008 to 0.025" inches (0.203–0.406 mm), with a smaller diameter wire being utilized for the smaller diameter grafts. For example, 0.012 to 0.016 inch (0.305–0.406 mm) diameter wire for the frame and wall engaging members may be used in the larger grafts of eighteen to twenty-eight millimeters diameter, and 0.008 to 0.012 inch (0.203–0.305 mm) diameter wire may be used in the smaller grafts being eight to sixteen millimeters in diameter.

It has been found that the spring force created by the helical torsion springs at the apices is largely determined by the diameter of the wire. The greater the diameter of the wire, the greater the spring force applied. Also, the longer the distances are between the apices, the smaller the spring force that is applied to the legs. It therefore has been desirable to provide a spacing of approximately eighteen millimeters between the outer extremities of the legs of the superior attachment system 175. Similarly, a spacing of approximately ten millimeters between the outer extremities of the legs of the inferior attachment system 176 is preferable, although smaller or larger distances may be utilized.

FIG. 22 shows a low stress configuration of an attachment system. An additional helical torsion apex 185 is added along the legs of the attachment system. The additional apices are located adjacent the apices at the vees formed by the legs. Such a configuration improves the fatigue characteristics of the attachment system. In addition, the weld location for the welded attachment system may be moved down the attachment system leg to improve fatigue life. Alternatively, a non-round or non-circular wire, for example, a rectangular, conical or rounded ribbon wire, may be used to reduce the amount of stress in the attachment system and still maintain the spring force of the attachment system.

To facilitate securing the graft 55 in the corporeal lumen, the tips 405 of the wall engaging members 374 on the superior attachment system 175 may be angled with respect to longitudinal axis of the main tubular member 170. The wall engaging members face outwardly from the main tubular member to facilitate holding the graft in place. Preferably, the conical tips of the wall engaging members on the superior attachment system are inclined from the longitudinal axis and toward the inferior end of the graft by 55° to 90° and preferably about 85°. Likewise, the tips 195 of the wall engaging members 193 on the inferior attachment system 176 may be inclined towards the superior end of the graft by 30° to 90° and preferably 85°. By angling the conical tips of the wall engaging members so that they resist the force of the blood flow, the implanted wall engaging members oppose migration of the graft.

The helical torsion springs 180, 370, 400 placed at the apices of the attachment systems serve to facilitate compression of the graft 55 to place the superior and inferior attachment system 175 and 176 within the capsule assemblies 90, 130 and 200, as hereinafter described. The compression of the graft is accomplished by deformation of the helical torsion springs to just outside their elastic limit, thereby having a small component within the plastic range. Placing the apices in different planes and staggering or offsetting the wall engaging members 193, 374 significantly reduces the minimum compressed size of the graft. Having the tips 196, 399 in different planes also helps to prevent the wall engaging members from becoming entangled with each other. The natural spring forces of the helical torsion springs serves to expand the graft to its expanded position as soon as the attachment system is free of the capsules.

The graft 55 preferably contains a radiopaque marker system for locating the graft and for detecting any twisting of the graft during deployment. As shown in FIGS. 14–16, the preferred radiopaque marking system for a bifurcated graft 55 includes short and long radiopaque markers 256, 257 located longitudinally on the wall 173 of the graft in a line parallel to the longitudinal axis of the main tubular member 170 and located on opposite sides thereof. By having the short radiopaque markers on the side of the graft from which the contralateral leg extends and the long markers on the side of the graft from which the ipsilateral leg extends, for example, under flouroscopy, the proper orientation of the graft can be ensured. Elongate tubular leg marker coils 255 are sewn laterally within pre-determined valleys between crimps of the legs and on the same longitudinal axis as the long and short radiopaque markers 256 and 257. When detecting twist of the graft under fluoroscopy, the tubular leg markers appear with varying widths may appear lateral and medial to the guide wire in the leg. The tubular leg markers, however, appear uniform in size and lateral to the guide wire in the leg for a tubular leg that is not twisted.

Additionally, radiopaque markers are positioned at the point of bifurcation of the graft. These two aid in determining whether the graft is twisted.

The sizing of the graft 55 may be performed on a patient-by-patient basis, or a series of sizes may be manufactured to adapt to most patient needs. The tubular legs 172 and 171 are approximately of the same length in the preferred embodiment but may. Be staggered from 0.1 to 6 centimeters if configured on a patient by patient basis. For the repair of an arctic aneurysm, the hook to hook length of the prosthesis is selected so to span approximately one and one-half centimeter superior and two centimeters inferior of the aneurysm, wherein the wall engaging members of the graft can seat within normal tissue of the vessel on both sides of the aneurysm. Thus, the graft should be about two centimeters longer than the aneurysm being repaired. During the preimplant fluoroscopy procedure, a conventional pigtail angiography catheter is used to determine the locations of the renal arteries to ensure the renal arteries will not be covered by the implanted graft. Likewise, on the inferior end of the corporeal lumen, determining the location of the internal iliac arteries ensures that they will not be covered by the implanted graft. Also, the diameter of the main tubular member 170 is selected by measuring the corporeal lumen which will receive the graft by conventional radiographic techniques and then selecting a graft with a main tubular member and tubular legs 171 and 172 having a diameter at least 0.1 or one-tenth millimeter larger than that measured. In the preferred embodiment, the diameter of the tubular legs is half the diameter of the main tubular member which is available in two millimeter increments of 18 mm, 20 mm, 22 mm, 24 mm, 26 mm and 28 mm.

As shown in FIGS. 14–16 and 18, segments or tufts of polyester yarn 418 or similar material are sewn about the circumference of the graft 55. The segments or tufts 418 are used to produce a "fuzzy" thrombogenic surface to reduce blood leakage and improve blood clotting and coagulation along the superior end of the main tubular member 170. The filaments of the yarn segment are teased apart to increase the embolization area. The yarn segment is sutured to the wall 173 of the graft between the vees 177 of the superior attachment system 175.

Similarly, yarn segments may be attached to the graft wall adjacent the inferior attachment systems 176 on the ipsilateral and contralateral tubular legs 171 and 172. Alternatively, the graft may be made of velour or terry to similarly occlude blood flow through the ends of the graft adjacent the attachment system. Likewise, other modifications to the graft wall may be made to accomplish the same result.

FIGS. 1, 7, 8, 26 and 27 show the contralateral capsule assembly 200 comprising a contralateral capsule 202 and a guiding tube assembly 205. The purpose of the contralateral capsule is to retain the inferior attachment system 176 secured to the contralateral tubular leg 172. The guiding tube assembly is used to pull the contralateral capsule into the contralateral artery, e.g., iliac, and is configured to deploy the inferior attachment system when the contralateral tubular leg is properly positioned. The contralateral capsule is also configured to connect with a torque catheter 215 to aid in proper deployment of the contralateral tubular leg.

As shown in FIG. 26, the contralateral capsule 202 is of sufficient length to contain the contralateral inferior attachment system 176 secured to the contralateral tubular leg 172. The contralateral capsule prevents the conical tips 196 of the wall engaging members 193 from contacting the wall of the body lumen prior to deployment of the attachment system. The contralateral capsule is made from stainless steel or similar biocompatible material. The contralateral capsule is typically 2 centimeters long with a internal diameter of 0.3 centimeters. The contralateral capsule is preferably circular shaped so as to fit within the indentation of the proximal capsule 132, as shown in FIG. 25, and is open at its distal end to receive the inferior attachment system. In addition, the contralateral capsule may be configured with an indentation (not shown) to prevent the inferior attachment system from rotating within the contralateral capsule.

A barbed adapter 203 is fitted within the proximal end of the contralateral capsule 202 to couple to the distal end of the torque catheter 215. The barbed adapter is formed around a polyethylene guiding tube 206 which comprises the distal length of the guiding tube assembly 205. The distal end of the guiding tube is flared and expanded just distal of the barbed adapter. A retaining bump 204 may be formed on the guiding tube just proximal of the barbed adapter to secure the adapter in place. The barbed adapter is further configured with a bore in which the guiding tube resides. Furthermore, the barbed adapter is secured to the guiding tube with adhesive.

A distal lock set 208 is fixed at the distal end of a pull wire 207 spaced apart from a proximal sliding pusher button 209, each of which reside within the contralateral capsule. The distal lock set 208 is configured with a 0.028" outer diameter, stainless steel fixed guidewire which extends into the trunk or main tubular member 170 preferably 1.2 centimeters distal of the graft bifurcation marker 255. The length of the lead wire may range from 4 centimeters to 15 centimeters depending on the length of the contralateral tubular leg 172. Proximal to the sliding pusher button 209 is a stop 199 which limits the proximal motion of the pusher button. The hypotube stop 199 is crimped to the pull wire 207. Prior to deployment of the contralateral tubular leg 172 into the contralateral iliac artery, the inferior attachment system 176 resides in the contralateral capsule between the distal lock set and proximal pusher button.

The guiding tube assembly 205 comprises the pull wire 207 disposed within the distal guiding tube 206 and a proximal guiding tube 213. Approximately a distance equal to the length of the graft 55 from the contralateral capsule 202, or distal end of the guiding tube, a six centimeter segment of the guiding tube is configured with a radiopaque material, such as a platinum coil 210. As shown in FIGS. 1, 7 and 8, the radiopaque material marks the point where the guiding tube exits the distal end 163 of the capsule jacket 160. Moreover, a pre-determined number of spaced-apart platinum radiopaque markers 420 (preferably ten in number) are positioned on the guiding tube assembly 205 proximally relative to the platinum coil 210. Such markings allow fluoroscopic determination of whether the guiding tube has been twisted, kinked, or wrapped around the capsule jacket or distal capsule assembly 90 as well as the longitudinal position of the guiding tube within the vasculature.

The guiding tube assembly 205 is further configured with a tapered joint 211 approximately fifty centimeters from the contralateral capsule 202. The tapered joint connects the distal guiding tube 206 with a proximal guiding tube 213. The tapered proximal end of the distal guiding tube nests inside the flared distal end of the proximal guiding tube. Both guiding tubes are preferably made from polyethylene tubing or similar material. The proximal end of the proximal guiding tube is connected to a 0.035 inch (0.9 mm) diameter contralateral "J-tipped" guide wire 212 made from stainless steel and having a length of about seventy centimeters.

The pull wire 207 extends from the contralateral capsule 202 to a point just proximal the proximal end of the proximal guiding tube 213. The pull wire is fixed at its proximal end to the proximal guiding tube to prevent relative movement between the parts of the guiding tube assembly 205 such that pulling on the contralateral guide wire 212 or the proximal guiding tube will cause corresponding movement of the contralateral capsule. If, however, the guiding tube assembly 205 is cut at specific points between the tapered joint 211 and the contralateral guide wire, then the proximal portion of the proximal guiding tube can be removed from the pull wire. Once the assembly is cut, the contralateral capsule can be moved relative to the pull wire by sliding the distal guiding tube 206 proximally over the pull wire. Back or colored marker bands 214 formed from PET shrink tubing are positioned at predetermined locations on the proximal guiding tube 213 to indicate the chronological order in which the sections of the guiding tube assembly is removed during the deployment process. In the preferred embodiment, the guiding tube assembly has a single marker, a marker group with two marks and a marker group with three marks. The single marker is cut away to remove the "J-tipped" guide wire whereas the marker group with two marks is cut away to enable relative movement between the contralateral capsule and the pull wire.

A torque catheter assembly 215 for use with the contralateral capsule assembly 200 is shown in FIG. 27. The torque catheter assembly consists of a torque catheter shaft 216 made of a flexible plastic material, such as PEBAX. The shaft is of sufficient length to span the distance from the contralateral femoral cutdown or percutaneous 12 French introducer sheath to the position in the contralateral iliac artery where the contralateral attachment system 176 is to be deployed, for example, forty centimeters. The torque catheter shaft is provided with a through lumen configured to accept and pass over the proximal and distal sections 213 and 206 of the guiding tube assembly 205.

The distal end 217 of the torque catheter shaft 216 is configured to connect to the barb adapter 203 on the contralateral capsule 202. The distal end of the shaft is further configured with a radiopaque marker band 218 for use in securing the distal end of the torque catheter to the barb adapter. Alternatively, the distal end of the shaft may be configured with a radiopaque adapter configured to mate with the barb adapter. The distal end of the torque catheter shaft is preferably provided with one or more purge ports 219.

The proximal end 221 of the torque catheter assembly 215 is provided with a stop cock 222 having a female Luer fitting 223 for injecting a fluid for purging the torque catheter shaft lumen 220. Likewise, a contrast fluid may be injected through the Luer fitting and out the distal end 217 or purge ports 219 of the torque catheter shaft. The proximal end of the torque catheter shaft is further provided with a hemostatic seal 240 and a Touhy Borst adapter 241 separated by a single lumen polyethylene tube 242. Distal to the stop lock, the torque catheter is configured with a male luer adapter 410 which mates with a distal female luer fitting 411.

The hemostatic seal 240 locks on and seals the distal guiding tube 206 with the barb adapter 203 engaging the distal end 217 of the torque catheter shaft 216. The proximal Touhy Borst adapter 241 engages the proximal guiding tube 213 and ultimately the pull wire 207 which secures the contralateral attachment system 176 within the contralateral capsule. The tapered joint 211 between the distal guiding tube and the proximal guiding tube resides between the hemostatic seal and the Touhy Borst adapter. This engagement allows safe torque ability of the contralateral capsule 202 and adjustment of the position and orientation of the contralateral limb.

The ends of the polyethylene tube are configured with barbed male Luer fitting 243 on the distal end and a barbed female luer fitting on the proximal end 244 on which the hemostatic seal and Touhy Borst adapter 240, 241 are secured. To allow longitudinal movement of the contralateral limb, the guiding tubes 206 and 213 should have the hemostatic seal and Touhy Borst adapter locked.

FIG. 8 depicts the distal end of the intraluminal grafting system 50 assembled for deployment. The distal cap 92 is in its retracted or proximal position adjacent to proximal cap 100. Similarly, core wire 91 is locked via control knob 113 in its retracted or proximal position. During initial deployment, capsule catheter tubular member 131 is in its most distal position in relation to balloon catheter assembly 51 and is locked in place by the lever lock on the capsule catheter assembly.

The graft 55 is disposed within the distal capsule 93, the proximal capsule 132, the contralateral capsule 202 and the capsule jacket main sheath 160. The superior end of the main tubular member 170 and superior attachment system 175 are removably retained within the distal capsule 93. The inferior end of the ipsilateral tubular leg 171 and inferior attachment system 176 are removably retained within the proximal capsule 132. Likewise, the inferior end of the contralateral tubular leg 172 and inferior attachment system 176 are removably retained within the contralateral capsule 202.

During initial deployment, the distal end of the balloon catheter 80 is positioned such that the distal stem 82 of the balloon 60 resides within the main tubular member 170 of the graft 55, as shown in FIG. 8. The proximal cap 100 is positioned just proximal the distal cap 92 and is disposed within the distal capsule 93. In addition, proximal pusher button 86 and distal lock 87 are disposed on either side of the ipsilateral attachment system 176 within the proximal capsule 132. Similarly, proximal sliding pusher button 209 and distal lock set 208 are disposed on either side of the contralateral attachment system 176 within the contralateral capsule 202. In the preferred embodiment, distal pusher button 87 and distal set 208 are disposed just distal of the respective attachment systems 176. Also, the capsule jacket assembly 53 is longitudinally locked and positioned such that the distal end 163 of the capsule jacket main sheath 160 overlaps at least a portion of the distal capsule. During deployment, capsule jacket locking connector 162 secures the main sheath in place. Thus, when any movement or force is applied to the handle assembly 145, the entire apparatus 50 moves as a single unit. It is also contemplated that the handle assemblies 145 and 110 have socket head shoulder screws 246 opposite the knobs for an elastic vessel loop (not shown). The loop mounted on the posts function as a counting element to the quantity and direction of rotations made between the two handles in the correction for graft twist between the main tubular member and the tubular legs.

By way of example, the following describes a method of repair of an arctic aneurysm using the method comprising the present invention for intraluminal placement of a graft in an aorta. First, a patient is prepared in a conventional manner by use of a guide wire 56, a dilator and sheath (not shown) to access both ipsilateral and contralateral femoral arteries or vessels of the patient. In the preferred procedure, a super stiff 0.035" guidewire is used. The contralateral guide wire 212 is then used to feed the guiding tube assembly 205 through the cutdown in the ipsilateral femoral artery and ipsilateral iliac artery 228 into the aorta. By conventional means, a gooseneck snare catheter, basket catheter or similar device is fed through an introducer sheath emplaced in the contralateral femoral artery over a contralateral guidewire (not shown) to the contralateral iliac artery 229. The contralateral guidewire is then removed. Thereafter, the snare or basket catheter is used to snare or capture the J-tipped proximal end of the guiding tube assembly. The guiding tube 206 is then pulled through the contralateral iliac artery and out the cutdown or introducer sheath in the contralateral femoral artery.

The distal end of the intraluminal grafting apparatus 50 is then inserted into the sheath over the super stiff 0.035" guide wire, which has previously been placed in the femoral artery. In the preferred embodiment of the present invention, balloon catheter lumen 63 is provided for receiving the guide wire 56 that was previously traversed across the aneurysm. However, the following procedure may also be used when the guiding member is constructed as part of the balloon catheter.

Figure 28:
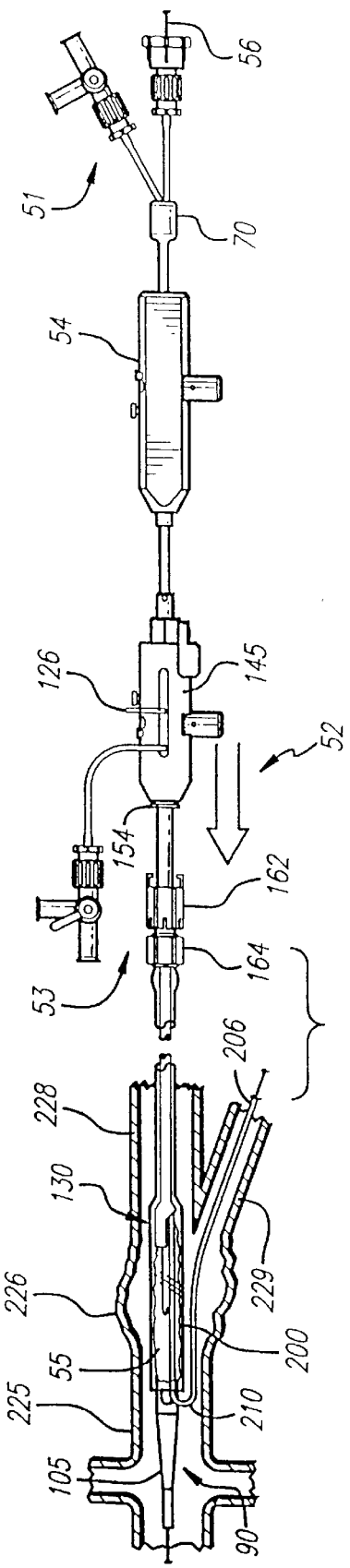
FIG. 28 is a partial cross-sectional view of the intraluminal grafting system shown positioned within the corporeal lumen.

Next, the balloon catheter assembly 51, the ipsilateral capsule catheter assembly 52, the capsule jacket assembly 53 and the control wire assembly 54 are all configured for deployment as shown in FIGS. 1 and 8. Thus, the assemblies may be advanced by the physician as a single unit over the main guide wire 56. As shown in FIG. 28, the main guide wire is introduced by the physician into an arteriotomy or introducer sheath in the ipsilateral femoral artery and advanced through the ipsilateral iliac artery 228 to the desired location in the abdominal aorta 225 and adjacent to the diseased or damaged portion 226 of the vessel.

The physician advances the distal end of the intraluminal grafting assembly 50, through the ipsilateral femoral artery over the guide wire 56, the nose cone 105 facilitating advancement about arduous turns, while maintaining slight tension on the guiding tube assembly 205 from the access site in the contralateral femoral artery. Typically, the desired position for implanting the graft 55 will be within the abdominal aorta 225 with the superior extremity of the main tubular member 170 at least one millimeter inferior to the lower renal artery. The inferior attachment systems 176 should be positioned superior the internal iliac arteries. Alternatively, the attachment system may be deployed in the common iliac below the internal iliac artery for one leg without additional surgical intervention or if both attachment systems are in the common iliac, additional surgical intervention is necessary to provide blood flow into the internal iliac. However, prior to removing the contralateral tubular leg 172 from the capsule jacket assembly 53, the proximal capsule assembly 130 and contralateral capsule assembly 200 must be positioned superior the bifurcation of the abdominal aorta to the ipsilateral iliac artery 228 and contralateral iliac artery 229, as shown in FIG. 28. Fluoroscopy is used to inspect the position of the radiopaque section 210 of the guiding tube assembly 205 to identify its longitudinal position within the vasculature as well as to ensure that the distal end of the guiding tube 206 is not wrapped or twisted around the distal capsule assembly 90 as the distal capsule 93 first enters the aorta.

Figure 29:
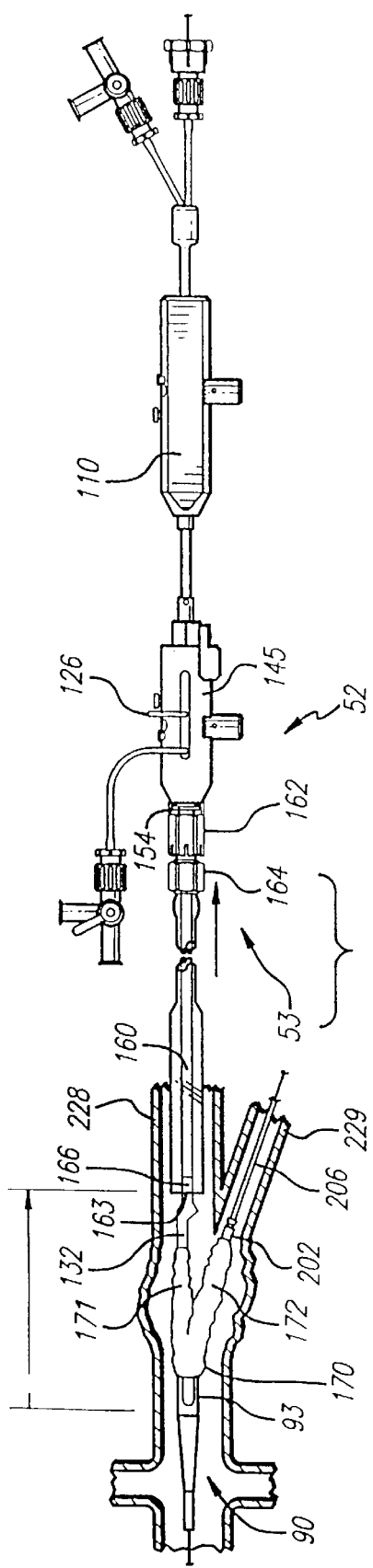
FIG. 29 is a partial cross-sectional view of the intraluminal grafting system, wherein the capsule jacket has been withdrawn from the graft.

When the proximal capsule assembly 130 and the contralateral capsule assembly 200 are in the desired position, the J-tipped end of the guiding tube assembly is discarded by cutting away the first marker 214 and for the purpose of maintaining a sterile field. Thereafter, as shown in FIG. 29, the locking ring 165 of the capsule jacket assembly 53 is loosened to allow movement of the capsule jacket main sheath 160. While using one hand to firmly grasp the ipsilateral capsule catheter assembly 52 and hold it stationary, the physician grasps the sheath adapter 164 with the other hand and gently pulls the sheath adapter proximally towards the capsule catheter wye adapter 145. Simultaneously, the physician applies slight tension on the guiding tube assembly 205 from the contralateral side as it is removed from the capsule jacket assembly. The capsule jacket assembly is gradually retracted to sufficiently expose the proximal capsule 132 to free the contralateral capsule 202. The capsule jacket assembly is then moved to its most proximal position and its proximal end 162 is locked to the male component 154 of the ipsilateral capsule handle 145. The locking ring is then tightened to hold the capsule jacket assembly in place, as shown in FIG. 29. The radiopaque marker 166 at the distal end of the capsule jacket main sheath may be used to position the capsule jacket as desired. Moreover, the position of the distal capsule 93 relative to the proximal capsule 132 is adjusted by using the marker bands on the hypotube 115 to adjust the graft 55 length to physiologic length.

Figure 30:
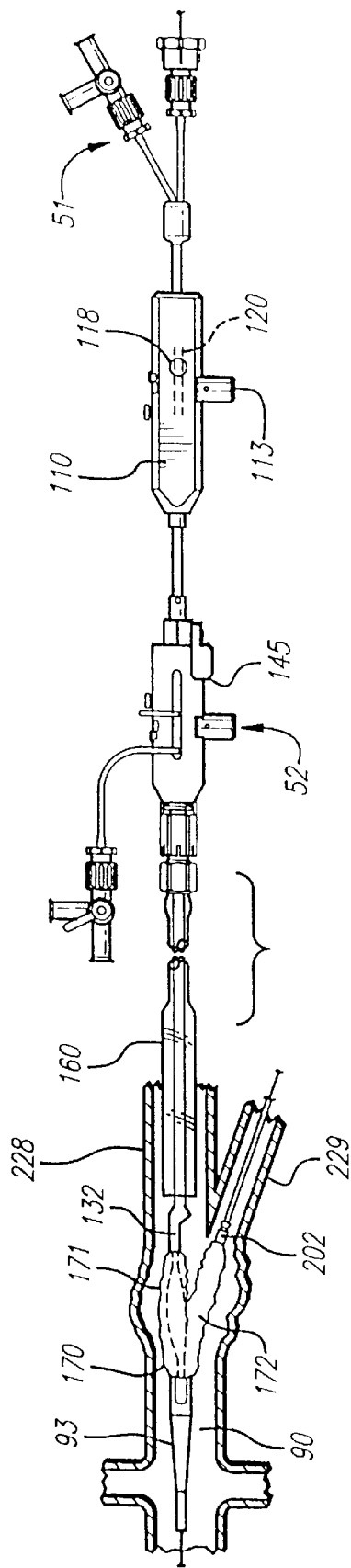
FIG. 30 is a partial cross-sectional view of the intraluminal grafting system, wherein the contralateral and ipsilateral tubular leg and contralateral and ipsilateral capsule assembly have been pulled into the respective iliac artery.

At this point in the procedure, the contralateral tubular leg 172 of the graft 55 is moved into the contralateral iliac artery 229 by pulling the guiding tube 206 in a proximal direction, as shown in FIG. 30. At the same time and with concurrent motion, the superior end of the main tubular member 170, disposed in the distal capsule 93, is moved into the desired location of the aorta 225 by moving the control handle 145, and thereby the intraluminal grafting assembly 50, in a proximal direction. By this motion, the inferior end of the ipsilateral tubular leg 171, securely retained within the proximal capsule 132, is moved to the desired location in the ipsilateral iliac artery 228 for deploying the ipsilateral attachment system 176. Similarly, the inferior end of the contralateral tubular leg, securely retained with in the contralateral capsule 202, is positioned for deployment of the contralateral attachment system. In order to insure proper orientation of the graft, the balloon catheter shaft lock can be disengaged and the superior capsule handle 110 rotated relative to the ipsilateral capsule catheter assembly 52 to maximize the lateral radiopaque marking on the graft. Once these steps are performed, each of the attachment systems should be in position for deployment.

The retaining screw 118 is loosened and the control knob 113 is then rotated to cause relative movement between the distal capsule assembly 90 and the balloon catheter assembly 51 to release the superior end of the main tubular member 170 and superior attachment system 175 from the distal capsule 93. Rotating the control knob causes the retaining rack 120 to move the control wire 91 in a distal direction. Since the distal cap 92, nose cone 105, and distal capsule 93 are secured to the control wire 91, and since the handle incorporates the coaxial design, they move in a precise manner and in corresponding relationship with the rotation of the control knob. As the distal capsule is moved from engagement with the superior attachment system, the balloon catheter proximal cap 100 locates at the proximal end of the distal capsule. The distal capsule is continued to be advanced so that a smooth profile of the superior capsule and the cap is achieved. As soon as the distal capsule has cleared the superior attachment system 175, the superior extremity of the main tubular member expands outwardly under the force of the self-expanding attachment system which springs into engagement with the vessel wall 230. The locking pin 126 holds the control knob, and thus the control wire and distal capsule, fixed in place.

Once the superior attachment system 175 is exposed, steps are taken to firmly seat or urge the wall engaging members 374 in the vessel wall. First, the collet lock assembly 158 on the ipsilateral capsule handle is loosened to permit relative movement between the ipsilateral capsule catheter assembly 52 and the balloon catheter assembly 51. While the physician uses one hand to hold the ipsilateral capsule catheter assembly stationary, the handle assembly 110 is grasped by the other hand and pushed distally to position the center of the main balloon 60 into the superior extremity of the main tubular member 170. The radiopaque marker 84 is used to align the main balloon and superior attachment system. The balloon shaft 61 is then locked again by activation of the collet lock assembly.

Figure 31:
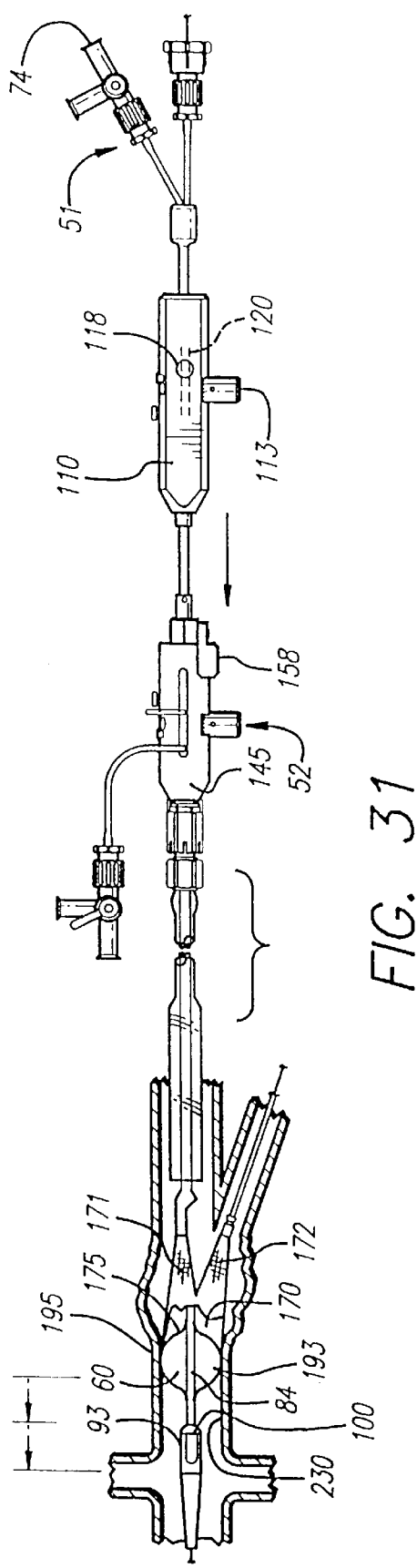
FIG. 31 is a partial cross-section view of the intraluminal grafting system, wherein the distal capsule has been removed from the superior end of the main tubular member and the inflatable member has been expanded to seat the superior attachment system.

Thereafter, a conventional hand operated syringe or inflation assembly (not shown) is attached to the balloon catheter inflation port 74. As depicted in FIG. 31, the main balloon 60 is then expanded by introducing a suitable gas such as carbon dioxide or a dilute radiopaque liquid from the syringe to urge the wall engaging members 193 outwardly to firmly emplace the superior conical tips 195 into the vessel wall 230. The main balloon may be deflated and inflated repeatedly to ensure the superior attachment system is firmly implanted in the vessel.

The main balloon 60 normally remains in an inflated position during the next steps of the procedure. During the actual retraction of the contralateral capsule 202 and proximal capsule 132, the main balloon should be inflated, further securing the superior attachment system 175. However, the main balloon may be deflated and reinflated during the following steps to allow the tubular legs 171 and 172 to fill with blood to facilitate detecting any twisting of the bifurcated graft 55.

Figure 32:
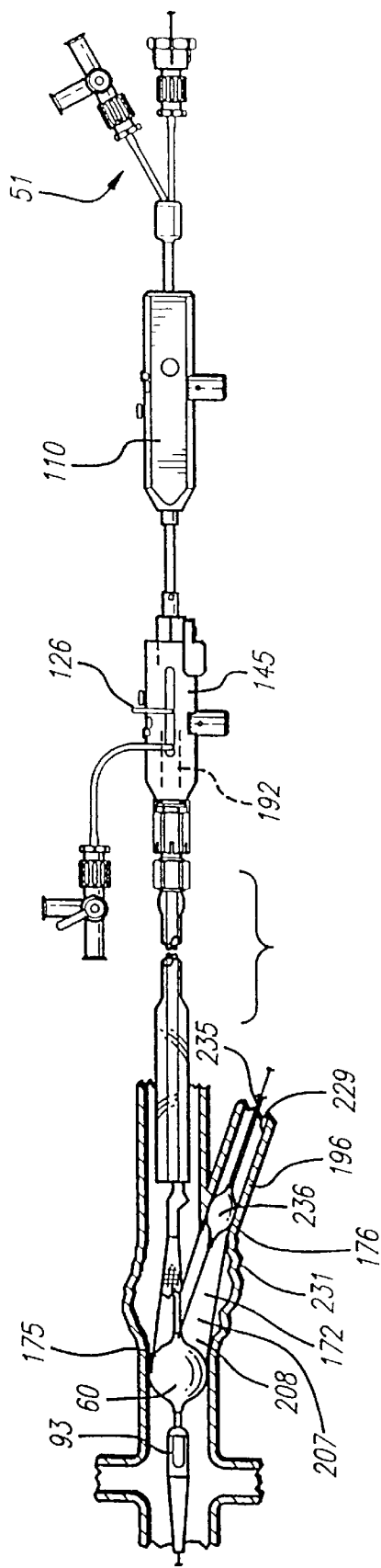
FIG. 32 is a partial cross-sectional view of the intraluminal grafting system, wherein the contralateral capsule has been removed from the inferior end of the contralateral tubular leg and an auxiliary balloon catheter has been positioned and inflated to seat the inferior attachment system.

As shown in FIG. 32, the next step is to implant or anchor the inferior attachment system 176 of the contralateral tubular leg 172. Then, the torque catheter assembly 215 is passed over the remaining guiding tube assembly 205 so as to engage the distal connector 217 of the torque catheter with the barb adapter 203 of the contralateral capsule assembly 200, as depicted in FIG. 24. The hemostatic seal 240 and Touhy Borst 241 is then tightened around the guiding tube assembly, thereby locking it in place and providing a seal. Thereafter, the torque catheter is used to straighten any twists in the guiding tube and can be used to adjust the placement of the contralateral capsule 202. The torque catheter may remain secured to the contralateral capsule assembly during the following procedure with the hemostatic seal 240 and Touhy Borst adapters 241 locked to the distal and proximal guiding tubes 206 and 213.

Next, the guiding tube assembly 205 is cut to disconnect the group containing two marker bands 214 to allow relative movement between the distal section of the guiding tube 206 and the pull wire 207. The Touhy Borst adapter 241 of the torque catheter assembly 215, which is locked to the proximal guiding tube, is disengaged by removing the Luer fitting 243 from the hemostatic seal 240 thereby exposing the pull wire 207. Thus, the proximal guiding tube 213 having the triple marker band is also removed. At this point, the contralateral leg 172 can be affixed within the iliac in either compression or in tension. To deploy the limb in compression, the contralateral lock wire is held fixed while the torque catheter is retracted over it. The contralateral pusher button 209 supports the attachment system 176 while the torque catheter is retracted keeping the attachment system fixed relative to the implantation site. To deploy the limb in tension, the torque catheter is retracted to release the attachment system attempting to keep the contralateral lock within the graft limb.

Once the inferior extremity of the contralateral tubular leg is free of the contralateral capsule, the inferior attachment system will spring open and the wall engaging members 193 will engage the contralateral iliac artery wall 231.

Thereafter, the torque catheter 215 and/or guiding tube 206 and contralateral capsule 202 are removed through the contralateral femoral artery access. The pull wire 207 may be moved distally so that the locking ball 208 is disposed near the superior end of the contralateral tubular leg 172. A conventional (contralateral) small nose balloon catheter 235 (FIG. 32) is then moved into the contralateral iliac artery 229 over the pull wire 207 and advanced until its tip engages the slidable pusher button 209 and causes it to abut the distal lock set 208. The stub nose balloon catheter is configured with a radiopaque marker in order to position the tip as desired using fluoroscopy. Then, the tip of the stub nose balloon catheter is positioned within the inferior attachment system 176. A contralateral balloon 236 configured on the contralateral balloon catheter is then inflated to firmly seat the tips 196 of the inferior attachment system into the contralateral iliac artery wall 231. The contralateral balloon may be deflated and reinflated throughout the contralateral tubular leg to open the entire length of the tubular leg. The contralateral balloon catheter remains in place with the contralateral balloon inflated during the next sequence of steps; however, the contralateral balloon catheter and pull wire may be removed once the contralateral attachment system is firmly implanted.

Figure 33:
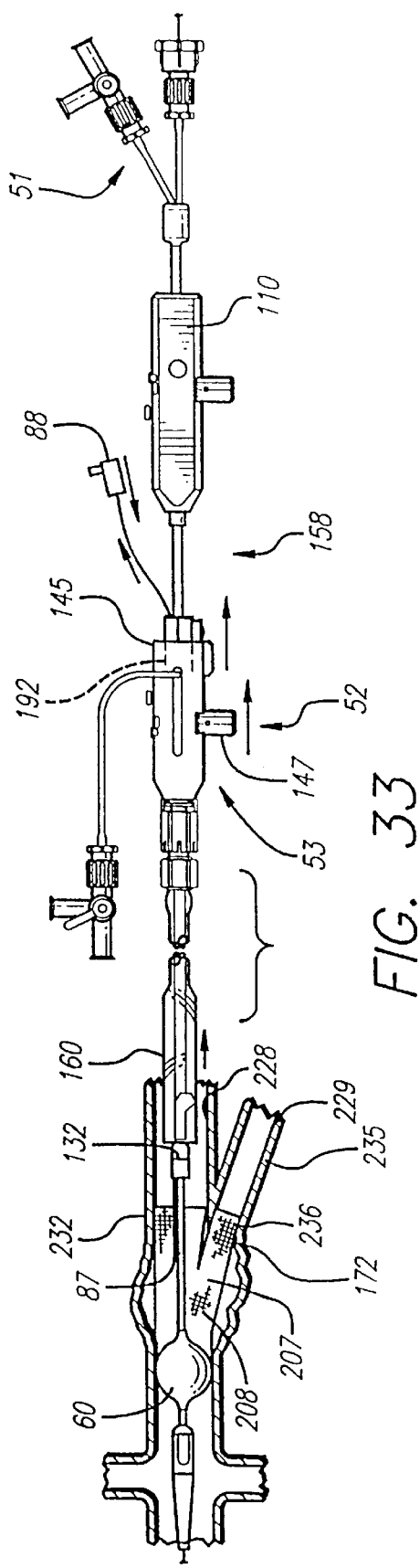
FIG. 33 is a partial cross-sectional view of the intraluminal grafting system, wherein the ipsilateral capsule has been removed from the inferior end of the ipsilateral tubular leg, releasing the ipsilateral inferior attachment system into the ipsilateral iliac artery.

As shown in FIG. 33, the next step is to deploy the inferior attachment system 176 of the ipsilateral tubular leg 171 into the ipsilateral iliac artery 228. The retaining pin 126 is removed from the ipsilateral capsule handle 145. The collet locking assembly 158 of the ipsilateral capsule handle 145 is locked to the balloon catheter. Then the control knob 147 is turned in order to effect longitudinal movement of the ipsilateral capsule 132 and rack 192, precise control of which is achieved by way of the coaxial design of the handle. The ipsilateral tubular leg 171 can be affixed within the vessel either in compression or tension. To deploy the limb in compression, the pusher button 86 and lock 87 remain locked longitudinally to the ipsilateral handle 145. The handle assembly 110 is also longitudinally locked to the ipsilateral handle 145 with the balloon 60 inflated to secure the superior attachment system, while the capsule catheter rack 192 is moved proximally when the knob 147 is rotated until the inferior attachment system and inferior end of the ipsilateral tubular leg are completely clear of the proximal capsule 132 while its position is held fixed relative to the corporeal lumen. To deploy the limb in tension, both the ipsilateral locking wire 87 and pusher button 86 and the capsule catheter assembly 52 are moved proximally until the leg 171 is held in tension. Thereafter, the capsule catheter assembly is moved further proximally while keeping the lock and pusher button stationary.

Whether deploying the ipsilateral tubular leg 171 in compression or in tension, once the inferior extremity of the limb is free of the proximal capsule 132, the ipsilateral inferior attachment system 176 will spring open and the wall engaging members 193 will engage the ipsilateral iliac vessel wall 232. Leaving the main balloon 60 inflated while the ipsilateral capsule catheter assembly 52 is moved ensures that the superior attachment system 175 will remain firmly secured in place. Thereafter, the main balloon 60 is deflated. The ipsilateral handle 88 is rotated 90° and retracted to release engagement with the ipsilateral handle 145 to position the lock 87 and pusher button 86 back within the ipsilateral capsule 132 for a smooth transition. As shown in FIG. 34, the handle assembly 110 is moved proximally so that the main balloon is retracted into the ipsilateral tubular leg 171 and placed adjacent the ipsilateral inferior attachment system 176. If the main balloon cannot be positioned adjacent to the ipsilateral attachment system due to limited available movement of the handle assembly, then the collet lock assembly 158 is secured to the hypotube 115, thereby securing the ipsilateral capsule catheter assembly to the balloon catheter assembly 51. The entire deployment catheter 50 is then moved proximally to position the main balloon adjacent the ipsilateral attachment system.

The main balloon 60 may be inflated and deflated through the entire length of the main tubular member 170 and ipsilateral tubular leg 171 to ensure patency of the bifurcated graft 55. Again, the balloon radiopaque marker 84 is used to align the center of the main balloon with the ipsilateral attachment system 176. The balloon is then inflated just enough to expand the ipsilateral attachment system to tack down the wall engaging members 193 into the ipsilateral iliac artery vessel wall 232. Thereafter, the main balloon is finally deflated.

As shown in FIG. 35, the proximal capsule assembly 130 and balloon 60 are moved proximal the graft 55 and within the capsule jacket assembly 53. First the collet lock assembly 158 is loosened. Then, while holding the ipsilateral capsule catheter assembly 52 in place by grasping the handle 145 with one hand, the balloon catheter assembly 51 is moved proximally by gently pulling the handle assembly 110 with the other hand. Thus, the capsule catheter assembly and balloon catheter are in the same relative position as they were just prior to deployment (FIG. 8). Also, the proximal end 103 of the distal capsule 93 has been mated with the proximal cap 100 for smooth transition.

Finally, the capsule jacket locking ring 165 is loosened and the proximal end of the capsule catheter 162 is disengaged from the male member 154 and the distal end of the ipsilateral capsule handle 145. While holding the capsule jacket sheath adapter 164 in place, the balloon catheter assembly 51 and capsule catheter assembly 52 are moved proximally and in unison by gently pulling the handle 145 of the ipsilateral capsule catheter assembly. The catheter assemblies are moved until the distal end 163 of the capsule jacket main sheath 160 covers the proximal cap 100 or until the proximal capsule adapter housing 134 mates with the flared transition of the capsule jacket, thereby creating a smooth transition along the entire length of the intraluminal grafting apparatus 50. Thereafter, the balloon catheter assembly, ipsilateral capsule catheter assembly, capsule jacket assembly 53 and control wire assembly 54 are removed from the aorta through the femoral artery. The graft 55 and attachment systems 175 and 176 remain secured to the vessel walls 230, 231 and 232, thereby sealing the aneurysm 226 from blood flow.

When the intraluminal grafting apparatus 50 is removed from the ipsilateral iliac and femoral arteries, the main guide wire 56 remains in place in the vessels. A conventional (ipsilateral) auxiliary balloon catheter (not shown) is traversed over the main guide wire and positioned at the inferior end of the ipsilateral tubular leg 171 and within the ipsilateral attachment system 176. An ipsilateral auxiliary balloon on the ipsilateral auxiliary balloon catheter is inflated to firmly implant the conical tips 196 of the wall engaging members 193 into the ipsilateral iliac artery wall 232. The ipsilateral auxiliary balloon may be inflated and deflated along the entire ipsilateral tubular leg to ensure the tubular leg is completely open and to remove creases which may have set while the graft was loaded in the capsule jacket assembly. The tubular legs may be dilated using two balloon catheters being simultaneously inflated while adjacent to each other introduced through the ipsilateral and contralateral leg respectively for a "kissing balloon" technique. Thereafter, the ipsilateral auxiliary balloon catheter is removed. The main guide wire is removed from the ipsilateral femoral artery after a post implant angiogram, introducer sheaths are removed and the cutdowns are closed.

The entire procedure described herein can be observed under fluoroscopy. The relative positioning of the graft 55 and the balloon 60 can be readily ascertained by the radiopaque attachment systems 175 and 176, radiopaque locking mechanisms 87 and 208, radiopaque markers 255, 256, 257 provided on the graft, the radiopaque marker 84 on the balloon shaft 61 and the proximal cap 100. If any twisting of the graft has occurred between placement of the superior attachment system and the inferior attachment system, then the twisting can be readily ascertained by observing the series of graft markers. Adjustments to eliminate any twisting which may have occurred can be made before exposing the attachment systems by rotation of the balloon catheter 51, the ipsilateral capsule catheter assembly 52 or the contralateral capsule 205 via the torque catheter 215. Any excessive graft compression can be ascertained by observing the radiopaque markers under fluoroscopy. Adjustments to eliminate graft compression can be made before exposing the inferior extremity of the graft by applying tension on the ipsilateral capsule catheter assembly and torque catheter 215.

Additional attachment systems may be placed within the tubular legs for the purpose of further preventing kinking of the graft material in the tubular legs. These additional attachment systems are placed medial the ends of the ipsilateral and/or contralateral tubular legs. Such medial attachment systems may resemble the inferior or superior attachment systems, but the medial attachment system are preferably configured without wall engaging members. The medial attachment systems are deployed using an auxiliary capsule catheter traversed over the main guide wire 56 and the contralateral pull wire 207 or another guide wire inserted in the contralateral tubular leg 172 after the contralateral attachment system 176 is firmly seated.

Post implant fluoroscopy procedures can be utilized to confirm the proper implantation of the device by the use of a conventional pigtail catheter or by injecting dye into the guide wire lumen of the balloon catheter shaft. Thereafter the sheath can be removed from the femoral artery and the femoral artery closed with conventional suturing techniques. Tissues should begin to grow into the graft within two to four weeks with tissue completely covering the interior side of the graft within six months so that no portion of the graft thereafter would be in communication with the blood circulating in the vessel. This establishes a complete repair of the aneurysm which had occurred. While several particular forms of the invention have been illustrated and described, it will be apparent that various modifications can be made without departing from the spirit and scope of the invention. For example, references to materials of construction and specific dimensions are also not intended to be limiting in any manner and other materials and dimensions could be substituted and remain within the spirit and scope of the invention. Accordingly, it is not intended that the invention be limited, except as by the appended claims.

What is claimed is:

1. A device for reorienting a graft at least partially implanted within vasculature, comprising:

an elongate shaft having first and second end portions; and a releasable connection device attached to said first end portion, said releasable connection device configured to be operatively attached to the graft at least partially implanted within vasculature;

wherein said second end portion is configured to be manipulated by an operator to effect reorientation of the graft.

2. The reorienting device of claim 1, said shaft further comprising a through lumen.

3. The reorienting device of claim 2, said second end portion further comprising a hemostatic seal.

4. The reorienting device of claim 3, wherein said shaft is configured with a plurality of purge ports in fluid communication with said through lumen.

5. The reorienting device of claim 2, wherein the graft is attached to a catheter assembly.

6. The reorienting device of claim 5, wherein said through lumen is adapted to receive said catheter assembly and said releasable connection device is adapted to releasably engage a portion of said catheter assembly.

7. The reorienting device of claim 1, wherein said releasable connection device is a barb adapter.

8. The reorienting device of claim 1, wherein said releasable connector device is a radiopaque adapter.

9. The reorienting device of claim 1, said first end portion further comprising a radiopaque marker.

10. The reorienting device of claim 1, said second end portion further comprising a stop cock and a luer fitting.

11. A method for reorienting a graft at least partially implanted within vasculature using an elongate reorienting device having a first end portion configured with a releasable connection device and a second end portion configured to be manipulated by an operator, comprising the steps of:

advancing the reorienting device within vasculature to a site proximate the graft;

causing the first end portion to become operatively connected to the graft; and manipulating the second end portion to reorient the graft.

12. The method of claim 11, wherein the reorienting device includes a through lumen and a catheter assembly is attached to the graft, further comprising the steps of:

advancing the reorienting device over said catheter assembly; and causing the first end portion to releasably engage the catheter assembly.

13. The method of claim 1, further comprising the step of applying a torque to the second end portion.

14. The method of claim 11, wherein the first end portion further includes a radiopaque marker and further comprising the step of observing positioning of the reorienting device within vasculature by fluoroscopy.

15. The method of claim 12, wherein the second end portion is configured with a stop cock and the reorienting device is further configured with a plurality of purge ports, further comprising the step of injecting contrast fluid through the through lumen.

* * * * *

UNITED STATES PATENT AND TRADEMARK OFFICE
CERTIFICATE OF CORRECTION

PATENT NO.    : 6,235,050 B1
DATED         : May 22, 2001
INVENTOR(S)   : Dinah B. Quiachon et al.

It is certified that error appears in the above-identified patent and that said Letters Patent is hereby corrected as shown below:

<u>Column 32, claim 13,</u>
Line 13, change "1", to read -- 11 --.

Signed and Sealed this

Twenty-fifth Day of December, 2001

Attest:

JAMES E. ROGAN
*Attesting Officer*      *Director of the United States Patent and Trademark Office*